United States Patent [19]

Tsien et al.

[11] Patent Number: 5,134,232
[45] Date of Patent: Jul. 28, 1992

[54] FLUORESCENT INDICATOR DYES FOR ALKALI METAL CATIONS

[75] Inventors: Roger Y. Tsien, Berkeley, Calif.; Akwasi Minta, Eugene, Oreg.

[73] Assignee: The Regents of the University of California, Oakland, Calif.

[21] Appl. No.: 391,879

[22] Filed: Aug. 9, 1989

Related U.S. Application Data

[63] Continuation-in-part of Ser. No. 271,502, Nov. 14, 1988, abandoned.

[51] Int. Cl.$^5$ ............................................. C07D 273/08
[52] U.S. Cl. .................................... 540/467; 540/469
[58] Field of Search ................................ 540/467, 469

[56] References Cited

U.S. PATENT DOCUMENTS 4,597,903  7/1986  Gokel et al. ........................ 540/467
4,927,923  5/1990  Mathis et al. ...................... 540/469

Primary Examiner—Nicholas S. Rizzo
Attorney, Agent, or Firm—Phillips, Moore, Lempio & Finley

[57] ABSTRACT

The invention discloses fluorescent chelator compounds that are especially useful to monitor and measure cytosolic concentrations of alkali metal cations such as $Na^+$, $K^+$, and $Li^+$. The new compounds are comprised of: (1) crown ethers (that may or may not have substituent groups attached to the core carbons, but will always contain at least one core nitrogen) that are linked via the core nitrogen(s) to at least one (2) fluorophore that contains an additional heteroaromatic liganding center. In the currently preferred dye, SBFI, the core compound is crown ether 1,7-diaza-4,10,13-trioxacyclopentadecane and the heteroaromatic fluorophores are benzofurans that are linked to isophthalate groups. Selectivities for $Na^+$ over $K^+$ of about 20 are observed, resulting in effective dissociation constants for $Na^+$ of about 20 mM against a background of 120 mM $K^+$. Increasing [$Na^+$] increases the ratio of excitation efficiency at 330–345 nm to that at 370–390 nm with emission collected at 450–550 nm, so that ratio fluorometry and imaging work at the same wavelengths as used with the well-known $Ca^{2+}$ indicator fura-2. If the macrocyclic ring is increased in size to a 1,10-diaza-4,7,13,16-tetraoxacyclooctadecane, the chelators become selective for $K^+$ over $Na^+$. If the ring is decreased in size, for example to a 1,7-diaza-4,10-dioxacyclododecane, the chelators become selective for $Li^+$ over $Na^+$.

24 Claims, 6 Drawing Sheets

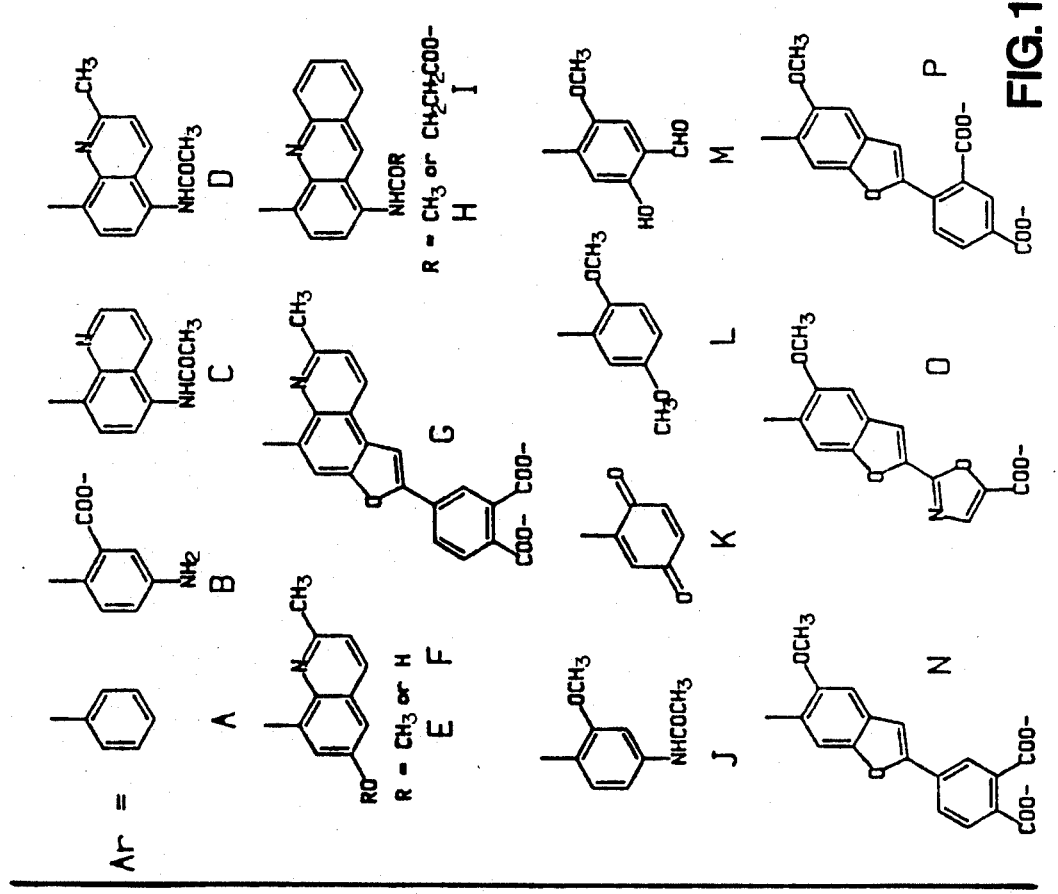
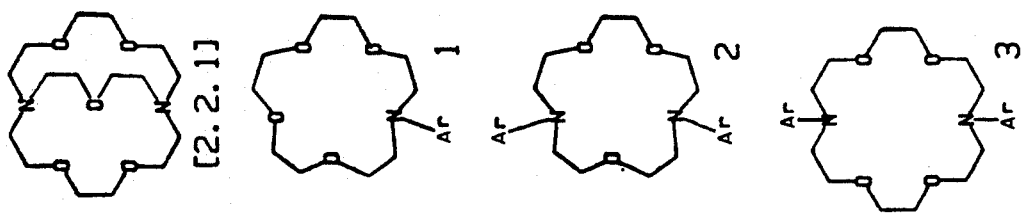
FIG. 1

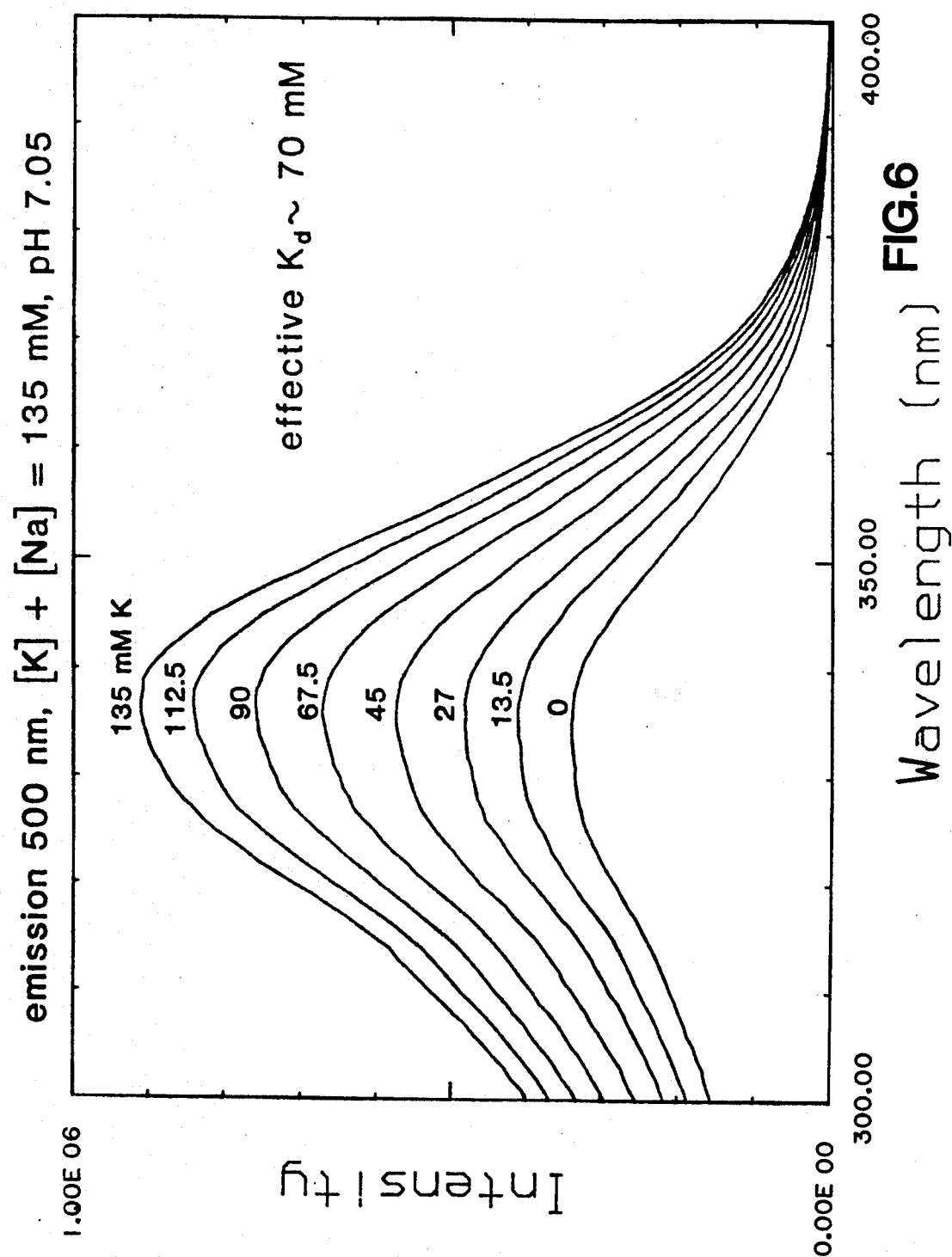

FLUORESCENT INDICATOR DYES FOR ALKALI METAL CATIONS

ACKNOWLEDGMENT

This invention was made with government support under Grant Contract No. GM-31004 awarded by the NIGMS and Grant Contract No. EY-04372 awarded by the NEI. The U.S. Government has certain rights in this invention.

This application is a continuation-in-part of U.S. Ser. No. 271,502 filed Nov. 14, 1988 now abandoned.

FIELD OF THE INVENTION

The present invention relates generally to new macrocyclic fluorescent chelating compounds for alkali metal cations. More specifically, the present invention relates to novel chemical compositions comprised of: the combination of (1) an aza-crown ether and (2) ligand(s), at least one of which will be a heteroaromatic fluorophore that bears additional cation chelating centers, wherein the ligand(s) is attached to the aza-crown ether via the sp$^3$-hybridized core nitrogen(s). The new fluorescent indicator compounds of the present invention are used to nondestructively observe concentrations of free alkali metal cations such as Na$^+$, K$^+$, and Li$^+$, particularly inside living cells and tissues.

BACKGROUND OF THE INVENTION

Nearly all animal cells maintain a large difference in sodium concentrations between their interiors (typically 10–40 mM) and the extracellular milieu (120–450 mM). This gradient is used to power nutrient uptake, epithelial transport, regulation of other intracellular ions, and transmission of electrical impulses. These functions are so important that organisms devote a major part of their metabolic energy to maintaining the sodium gradient (1,2).

Measurements of intracellular Na$^+$ are essential to understanding the many biological roles of this ion. Current techniques fall into three categories: (1) Assays that measure total cell Na$^+$ but destroy the tissue; (2) Non-destructive assays that rely on nuclear magnetic resonance; and (3) Non-destructive assays that rely on well-defined physiochemical equilibria to measure free [Na$^+$] or Na$^+$ activity.

Examples of assays that measure total cell Na$^+$ but destroy the tissue include flame photometry, atomic absorption, neutron activation, counting of $^{22}$Na at isotopic equilibrium, and electron microprobe analysis (30). The destructive nature of these techniques is obviously a drawback when time courses are desired. Except for the electron-microscopic methods, these techniques lack spatial resolution and demand careful removal of extracellular fluid, which usually has a much higher concentration of Na$^+$ than the cells. The most general problem (18,31,32) is that the total intracellular [Na$^+$] usually considerably exceeds free [Na$^+$]$_i$, and it is the latter that affects binding equilibria, transmembrane electrochemical gradients, and cell function. Free and total [Na$^+$] are known to be able to vary independently (32).

It is well known that NMR techniques using dysprosium shift reagents can quantify the amount of intracellular Na$^+$ that is readily exchangeable on the NMR time scale (33,34). This probably includes weakly bound Na$^+$ as well as free. Though non-destructive, this technique requires relatively large amounts of tissue packed at high density in a magnet cavity, an environment awkward for other manipulations.

Techniques that rely on well-defined physiochemical equilibria to nondestructively measure free [Na$^+$] (or Na$^+$ activity) include $^{19}$F MR of Na$^+$-sensitive chelators (6), Na$^+$-selective microelectrodes (32), and the new fluorescent indicators of the present invention. Advantages of fluorescent indicators include excellent spatial and unsurpassed temporal resolution, compatibility with cell types too small or fragile to impale with ion-selective and voltage reference barrels, and applicability to single cells as well as to populations (35). Perhaps the chief disadvantage is the demand for optical clarity of the tissue.

Prior art techniques for measuring and manipulating intracellular free sodium concentrations ([Na$^+$]$_i$) have been severely limited by the lack of synthetic ligands that can bind sodium with the requisite affinity and specificity in aqueous solution at pH 7. A particularly desirable ligand would have the following properties:

(1) Na$^+$ should bind with a dissociation constant ($K_d$) of 5–50 mM at pH 7, in aqueous solution with no organic co-solvents permitted. Such a $K_d$ would approximately match the expected range for [Na$^+$]$_i$ and maximize sensitivity to small changes in [Na$^+$]$_i$. Excessive Na$^+$ affinity would be undesirable, since the indicator would then either be Na$^+$-saturated and unresponsive, or if applied in excess would depress [Na$^+$]$_i$.

(2) The indicator should have enough discrimination against K$^+$ (at least twenty-fold, or a $K_d$>150 mM), H$^+$ (highest p$K_a$<6.5), Mg$^{2+}$ ($K_d$>10 mM), and Ca$^{2+}$ ($K_d$>10 µM) so that physiological variations in those ions have little effect.

(3) It would show reasonably strong fluorescence, characterizable by a product of extinction coefficient and fluorescence quantum yield exceeding $10^3 M^{-1} cm^{-1}$.

(4) Its excitation wavelengths should exceed 340 nm, because shorter wavelengths demand expensive quartz rather than glass microscope optics and are strongly absorbed by nucleic acids and aromatic amino acids.

(5) Emission wavelengths should exceed 500 nm to reduce overlap with tissue autofluorescence from reduced pyridine nucleotides peaking near 460 nm.

(6) Either the excitation or emission spectrum or both should undergo a large wavelength shift upon binding Na$^+$, so that ratioing of signals at two excitation or two emission wavelengths can cancel out the local pathlength, dye concentration, and wavelength-independent variations in illumination intensity and detection efficiency.

(7) The indicator should have enough polar groups such as carboxylates to render it highly water-soluble and impermeant through membranes, so that it does not rapidly leak out of cells.

(8) The polar groups just mentioned should be maskable by nonpolar protecting groups hydrolyzable by cytoplasm, so that large populations of cells can be loaded with the indicator by incubating them with the membrane-permeant nonpolar derivative rather than requiring microinjection or other techniques of membrane disruption. The most obvious protecting groups are acetoxymethyl esters, which have proven to be useful with a wide variety of cation indicators (51,52).

No such compound has yet been demonstrated to work in living cells despite nearly two decades worth of research on crown ethers and related ligands. Indicator dyes with visible absorbance and moderate preference for Na+ over K+ have been reported (3,4) but their operation is limited to nonaqueous solvents like acetonitrile, and no quantitative data is available on their cation binding constants. Higher affinity and selectivity for Na+ over K+ in water can be obtained with macrobicyclic chelators, for example the cryptand "[2.2.1]" (see ref. 5 and FIG. 1). Recently, fluorine-substituted cryptands have been introduced for measurement of [Na+]$_i$ by $^{19}$F-NMR (6). A promising fluorescent version was also described by Smith, et al., (1988) (see ref. 7), but its excitation and emission spectra peaked at rather short wavelengths, 320 and 395 nm respectively, and no demonstration of intracellular use was given. The highest selectivities for Na+ over K+ are obtained in very large rigid chelators called "spherands"; so far these require organic solvents for solubility and are so rigid that hours to days are required for equilibration with Na+ (8,9). The main mechanism by which they give optical shifts upon metal binding has been the displacement of a proton from the binding cavity, but this equilibrium must inherently be pH-sensitive, which is an unwanted feature. We chose to explore crown ethers rather than the more elaborate cryptands and spherands both for ease of synthesis and because of a concern that the conformational rigidity and preorganization of cryptands and spherands would tend to reduce the spectroscopic shift upon metal binding.

The present invention discloses a new series of macrocyclic compounds that can chelate alkali metal cations and that attain the basic goals described above for a desirable fluorescent sodium indicator. Tests in lymphocytes, hepatocytes, fibroblasts (10), smooth muscle cells (11), and gastric glands (12) demonstrate the biological utility of the macrocyclic compounds of the present invention for nondestructive observation of [Na+]$_i$ in individual cells viewed by fluorescence microscopy.

DESCRIPTION OF THE DRAWINGS

The drawings comprise 6 Figures, of which:

FIG. 1 is a drawing that shows the structures of some of compounds of the present invention. For comparison, Lehn's cryptand [2.2.1] (see ref. 5) is shown in the upper left hand corner. Below cryptand [2.2.1] are three generic types of crown ethers that have been prepared for use in the making some of the compounds of the present invention. To the right of the vertical dividing line are examples of some of the aromatic and heterocyclic substituents that can be attached to the nitrogens of the crown ethers. Compound "SBFI" is 2PP; "SBFO" is 2OO; "PBFP" is 3NN.

Dissociation constants, cation affinities, plus the absorbance and emission maxima and quantum efficiency for sodium are given in TABLE 1.

Figure 2:
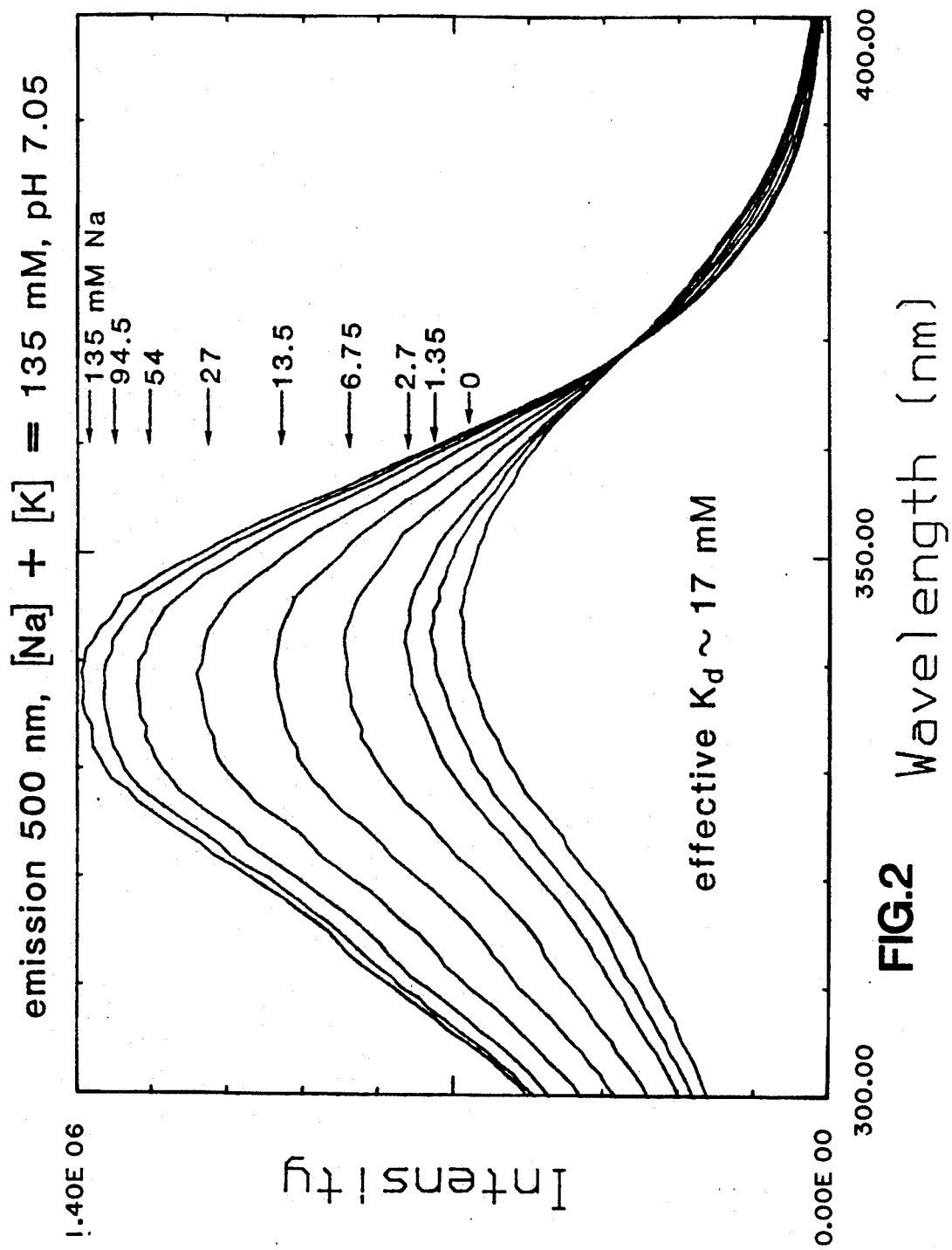

FIG. 2 is a graph that shows the fluorescence excitation spectra of SBFI as a function of increasing [Na+] and decreasing [K+]. The lowest curve ([Na+]=0) was obtained with 5 μM SBFI in 130 mM KCl, 10 mM MOPS, KOH to pH 7.05, approximately 135 mM total K+. The highest curve ([Na+]=135 mM) was analogously recorded from 5 μM SBFI in 130 mM NaCl, 10 mM MOPS, NaOH to pH 7.05. The intermediate curves from 1.35 to 94.5 mM Na+ were obtained by successively 1/100, 1/99, 3/98, 1/19, 1/9, ¼, and ½ of the K+-rich SBFI solution by the SBFI in Na medium. The excitation bandwidth was 1.85 nm; emission was collected at 500 nm with 9.3 nm bandwidth. The temperature was 22°, ±2°.

Figure 3:
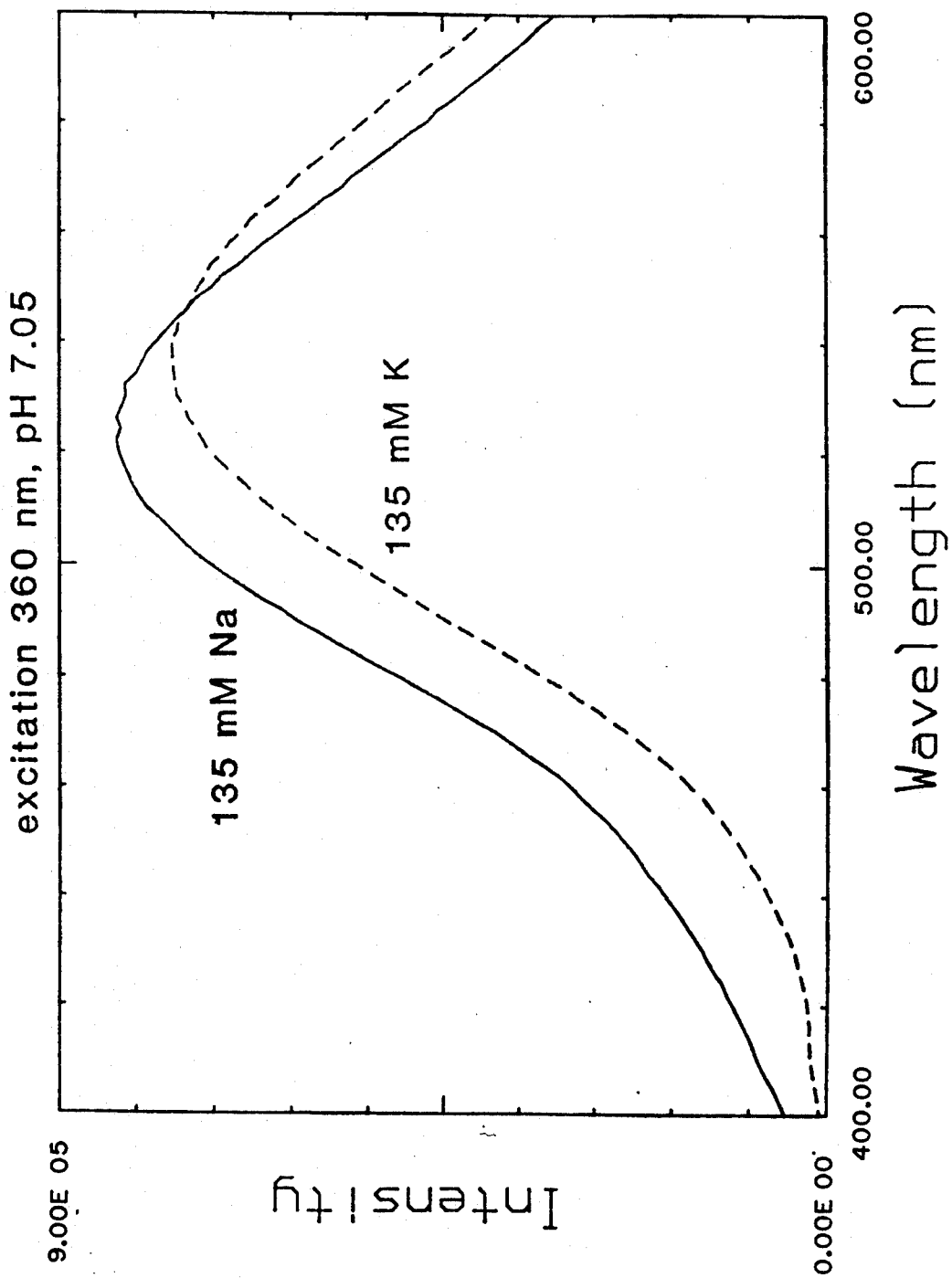

FIG. 3 is a graph that shows the fluorescence emission spectra of SBFI at 135 mM K+ and 135 mM Na+, recorded from the same solutions as used in FIG. 2 for 0 and 135 mM Na+. Excitation was at 360 nm; bandwidths were the same as in FIG. 2.

Figure 4:
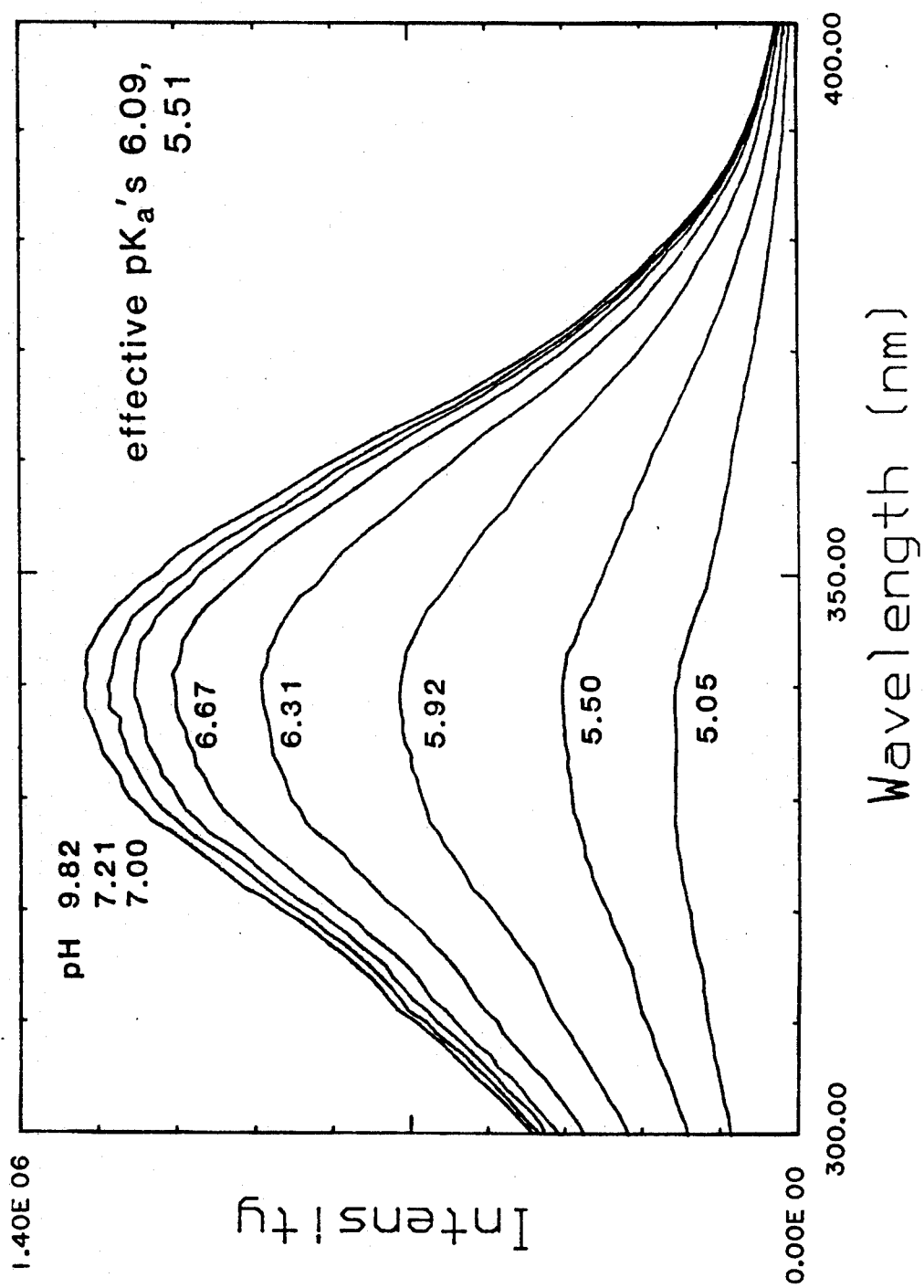

FIG. 4 is a graph that shows the fluorescence emission spectra of 5 μM SBFI in 14 mM NaCl, 126 mM KCl, 1 mM MgCl$_2$, 4 mM Tris, titrated to the indicated pH values by small additions of 5M H$_3$PO$_4$. Emission was collected at 530 nm. Bandwidths and temperature were as in FIG. 2.

Figure 5:
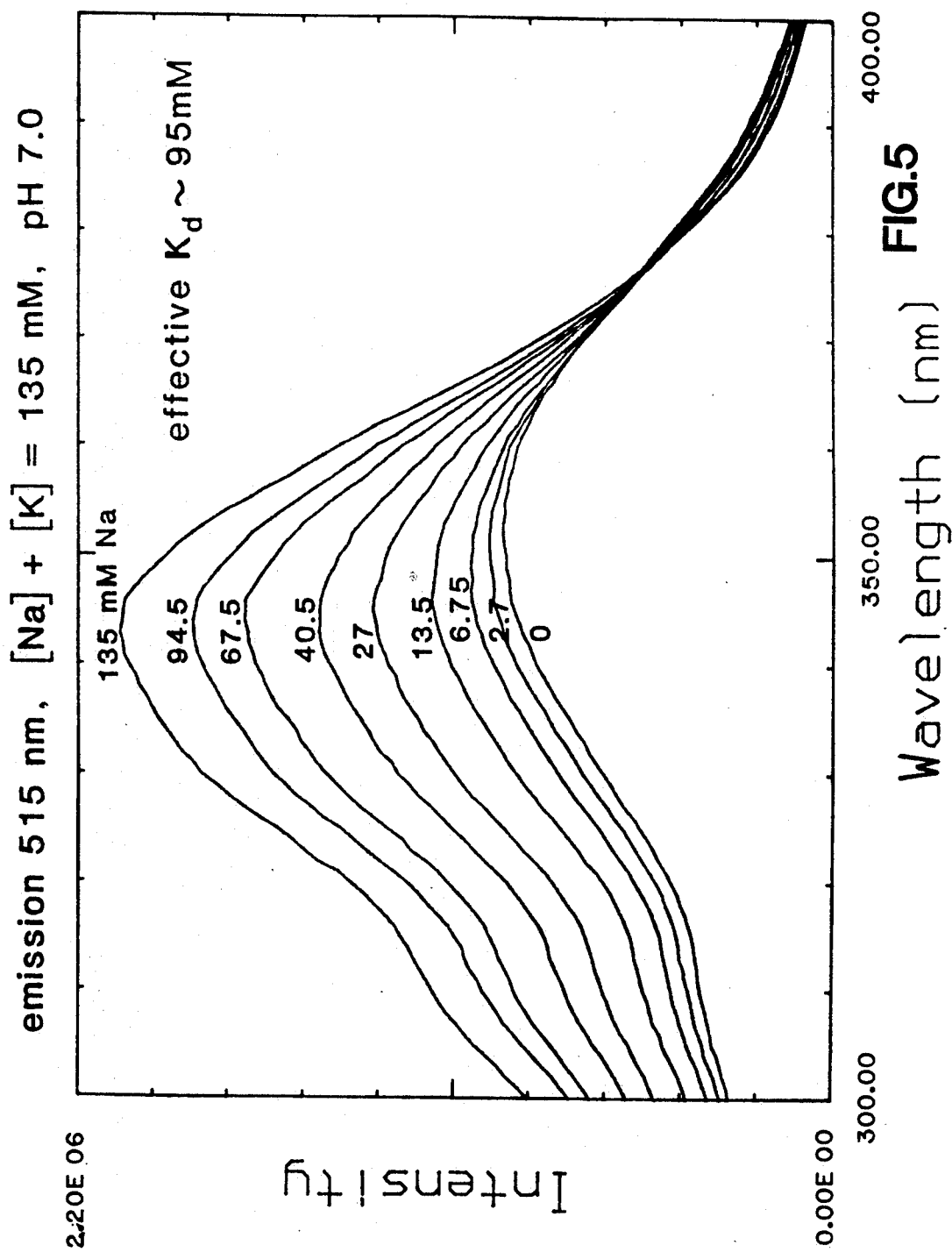

FIG. 5 is a graph that shows the fluorescence excitation spectra of 6 μM SBFO as a function of increasing [Na+] and decreasing [K+] in solutions similar to those in FIG. 2. The intermediate Na+ concentrations from 2.7 to 94.5 mM were obtained by the iterative replacement of 1/50, 3/98, 1/19, 1/9, ¼, 2/7, and 2/5 of the high K+ medium by the 135 mM Na mixture. Excitation bandwidth was 1.85 nm; emission was collected at 515 nm and 4.7 nm bandwidth.

FIG. 6 is a graph that shows the fluorescence excitation spectra of 10 μM PBFP as a function of increasing [K+] and decreasing [Na+] in solutions similar to those of FIG. 2. The lowest curve was obtained in 130 mM NaCl, 10 mM MOPS, NaOH to pH 7.05. The highest curve was in 130 mM KCl, 10 mM MOPS, KOH to pH 7.05. The intermediate curves with 13.5 to 112.5 mM K+ were obtained by iteratively replacing 1/10, 1/9, 1/6, ¼, ⅓, and ½ of the low K+ medium by the 135 mM KCl solution of PBFP.

DEFINITIONS

In the present specification and claims, reference will be made to phrases and terms of art which are expressly defined for use herein as follows:

As used herein, [Na+] means free sodium concentration, typically in a test solution.

As used herein, [Na+]$_i$ means intracellular free sodium concentration.

As used herein, crown ethers mean macromonocyclic polyethers with the repeating unit, (—CH$_2$—CH$_2$—Y—)$_n$, where Y is a heteroatom (e.g., O, S, N, P), and n is greater than 2. In the crown ethers that are useful in making the macrocylic fluorescent compounds of the present invention, the total number of atoms in the crown ring will be at least 12, but not greater than 18; n will be at least 4, but not greater than 6; n will be N or O, not S or P; and at least one Y will always be N. For examples that illustrate preparation of crown ethers, see C. J. Pedersen, J. Am. Chem. Soc., 89, 2495, 7017 (1967); also see U.S. Pat. No. 3,687,978, which issued to C. J. Pedersen in 1972. For other examples and reviews of the crown ethers, see D. J. Cram, J. M. Cram, Science, 183, 803–809 (1974); J. J. Christensen et al., Chem. Rev., 74, 351–384 (1974); G. W. Gokel, H. D. Durst, Synthesis, 168–184 (1976); A. C. Knipe, J. Chem. Ed., 53, 618–622 (1976); S. Kulstad and L. A. Malmsen, Acta Chemica Scandinavica, B 33, 469–474 (1979); Macrocyclic Polyether Synthesis, Gokel, G. W., and Korzeniowski, S. H., (Eds.), Springer Verlag, Berlin (1982); D. A. Laidler and J. F. Stoddart, in The Chemistry of Ethers, Crown Ethers, Hydroxyl Groups and Their Sulphur Analogues, Supplement E, part 1, (S. Patai, ed.), pp. 1–58, John Wiley, New York (1980); F. Vögtle, F., and E. Weber, ibid., at pages 59–156; Progress in Macrocyclic Chemistry, Izatt, F. M. and J. J. Christensen, J. J, (Eds.), a continuing series from J. Wiley, New York.

In another way, the compounds are described as a combination of:

(1) aza-crown ether and (2) ligand $L^1$ and optionally ligand $L^2$:

 

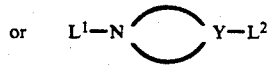

wherein at least one of $L^1$ and $L^2$ is a heteroaromatic fluorophore that bears an additional cation chelating center, wherein the ligand $L^1$ and $L^2$, when present, are covalently attached to the aza-crown ether via the sp$^3$-hybridized core nitrogens(s), and wherein:

(1) the crown ether is a macrocyclic polyether with the repeating unit, $(-CHR^{31}-CHR^{32}-Y-)_n$, wherein $R^{31}$ and $R^{32}$ are each hydrogen or at least one of $R^{31}$ and $R^{32}$ on the aza-crown ether core carbons is selected the group consisting of: —COOH, —CH$_2$OH, —C(=O)N(CH$_3$)$_2$, or C$_1$-C$_4$ alkyl and the other group is hydrogen; or $R^{31}$ and $R^{32}$ together are selected from the group consisting of —(CH$_2$)$_3$— and —(CH$_2$)$_4$—; $R^{31}$ and $R^{32}$ are part of an aliphatic system, or $R^{31}$ and $R^{32}$ together are —(CH)$_4$— and $R^{31}$ and $R^{32}$ are part of an aromatic system; or $R^{31}$ and $R^{32}$ on non-adjacent core carbons of the aza-crown ether together are selected from the group consisting of —(CH$_2$)$_2$— and —(CH$_2$)$_3$— and $R^{31}$ and $R^{32}$ are part of an aliphatic system, or $R^{31}$ and $R^{32}$ together are —(CH)$_3$— and $R^{31}$ and $R^{32}$ are part of an aromatic system.

As used herein, "aza-" is used generically to mean containing nitrogen, "monoaza-" is used more specifically to mean a crown ether that contains one nitrogen, "diaza-"]means containing two nitrogens, etc.

As used herein, when referring to the crown ethers, nomenclature lists non-ring substituents, ring substituents, number of atoms in the ring, the class (crown), and the number of heteroatoms in the ring. For example, diaza-15-crown-5-pyridinophane would be represented by the following formula (Note: In the structures, L means ligand):

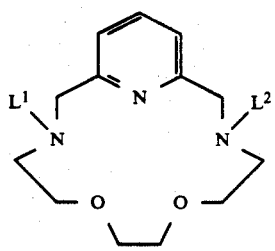

As used herein, when it is said that a diaza crown ether is "symmetrical" it means that the two nitrogens are located in positions as remote as possible from each other in the crowns. Examples of symmetrical diaza-18-crown-6 ethers would be 1,10-diaza-18-crown-6 or 1,7-diaza-15-crown-5. The formula for 1,7-diaza-15-crown-5 is given below.

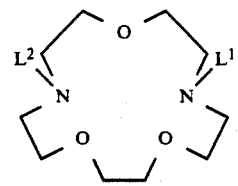

As used herein, when it is said that a diaza crown ether is "asymmetrical" it means that the two nitrogens are located in positions as close as possible to each other in the crown. Examples of asymmetrical crown ethers include: 1,4-diaza-15-crown-5, 1,4-diaza-18-crown-6, and 1,7-diaza-18-crown-6. The formula for 1,7-diaza-18-crown-6 is given below:

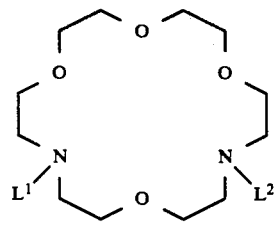

As used herein, "diaza[15]-crown-5" and "Kryptofix 21" mean the commercially available crown ether 1,7-diaza-4,10,13-trioxacyclopentadecane. Kryptofix 21 is available from Aldrich Chemical Company, Milwaukee, Wis. 53233.

As used herein, "Kryptofix 22" means the commercially available crown ether 1,10-diaza-4,7,13,16-tetraoxacyclooctadecane. Kryptofix 22 is available from Aldrich Chemical Company, Milwaukee, Wis. 53233 under the name "1,4,10,13-tetraoxa-7,16-diazacyclooctadecane.

As used herein, compounds are not always referred to by their chemical names. In some instances the compounds are referred to by their structures, i.e., the structures shown in FIG. 1. Such compounds are printed in bold. The compounds are named with a number and a letter, i.e., 1B where the number refers to the crown ether shown as structure 1, 2 or 3, and the letter refers to the substituents shown as structures A-P.

As used herein, compound "SBFP" means the compound whose structure is shown in FIG. 1 as 2NN, i.e., the combination of crown ether 2 and two N substituents. (SBFP has one N substituent attached to each of the two core nitrogens in crown ether 2.) "SBFP" is short for sodium-binding benzofuran phthalate. Both SBFP and 2NN are used herein to refer to this compound.

As used herein, compound "SBFO" means the compound whose structure is shown in FIG. 1 as 2OO, i.e., the combination of crown ether 2 and two O substituents. (SBFO has one O substituent attached to each of the two core nitrogens in crown ether 2.) "SBFO" is short for sodium-binding benzofuran oxazole. Both SBFO and 2OO are used herein to refer to this compound.

As used herein, compound "SBFI" means the compound whose structure is shown in FIG. 1 as 2PP, i.e., the combination of crown ether 2 and two P substituents. (SBFI has one P substituent attached to each of the two core nitrogens in crown ether 2.) "SBFI" is short for sodium-binding benzofuran isophthalate. Both SBFI and 2PP are used herein to refer to this compound.

As used herein, compound "PBFP" means the compound whose structure is shown in FIG. 1 as 3NN, i.e., the combination of crown ether 3 and two N substituents. (PBFP has one N substituent attached to each of the two core nitrogens in crown ether 3.) "PBFP" is short for potassium-binding benzofuran phthalate. Both PBFP and 3NN are used herein to refer to this compound.

As used herein, compound "PBFO" means the compound whose structure is shown in FIG. 1 as 3OO, i.e., the combination of crown ether 3 and two O substituents. (PBFO has one O substituent attached to each of the two core nitrogens in crown ether 3.) "PBFO" is short for potassium-binding benzofuran oxazole. Both PBFO and 3OO are used herein to refer to this compound.

As used herein, compound "PBFI" means the compound whose structure is shown in FIG. 1 as 3PP, i.e., the combination of crown ether 3 and two P substituents. (PBFI has one P substituent attached to each of the two core nitrogens in crown ether 3.) "PBFI" is short for potassium-binding benzofuran isophthalate. Both PBFI and 3PP are used herein to refer to this compound.

As used herein, when it is said that the "ligands" are attached to the aza-crown ether via the sp³-hybridized core nitrogen(s), it means that the ligands are attached via the nitrogen atomic orbitals that arise from the mixing of one s orbital and 3 p orbitals. See *Organic Chemistry*, Second Edition, R. T. Morrison and R. N. Boyd, Allyn and Bacon, Inc., Boston, (1970), at pages 10-18. An example of this kind of bonding is shown in the following formula for PBFI:

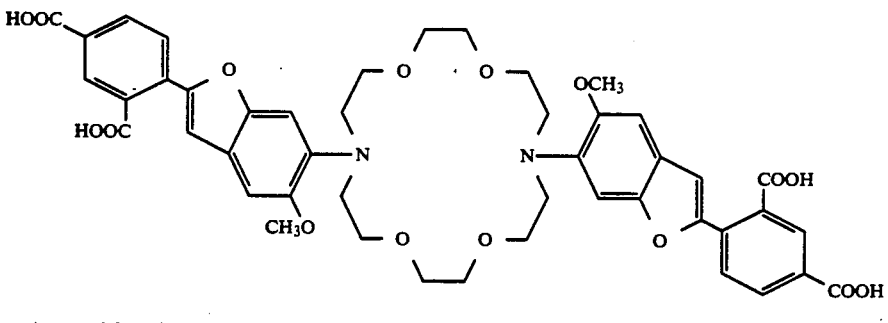

As used herein, when referring to the compounds of the present invention, when it is said that the "ligands" that are attached to the aza-crown ether (via the sp³-hybridized core nitrogen(s) of the aza-crown ether) "are identical", it means that the ligand attached to any one core nitrogen is the same as the ligand attached to any other core nitrogen. The formula shown above for PBFI is an example of a symmetric diaza-18-crown-6 having identical ligands attached to the two core nitrogens.

As used herein, when referring to the compounds of the present invention, when it is said that the "ligands" that are attached to the aza-crown ether (via the sp³-hybridized core nitrogen(s) of the aza-crown ether) "are different", it means that the ligand attached to any one core nitrogen is not the same as a ligand(s) attached to another core nitrogen(s). The following formula is an example of a diaza-18-crown-6 having different ligands attached to the two core nitrogens.

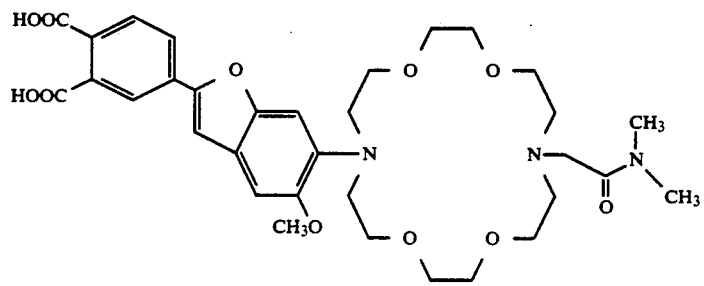

SUMMARY OF THE INVENTION

The present invention discloses new macrocyclic fluorescent chelating compounds for alkali metal cations. The new macrocyclic fluorescent chelating compounds are comprised of the combination of (1) an aza-crown ether and (2) ligand(s), at least one of which will be an aromatic or heteroaromatic fluorophore that bears an additional cation chelating center, wherein the ligand(s) is attached to the aza-crown ether via the sp³-hybridized core nitrogen(s).

In the compounds of the present invention, the crown ether is selected from the group consisting of: aza-12-crown-4, aza-15-crown-5 and aza-18-crown-6. According to the invention, the aza-crown ethers may be symmetric or asymmetric monoaza-, diaza-, triaza-, tetraaza-, pentaaza-, or hexaaza-crown ethers. Also according to the invention, at least one of the hydrogens on the core carbons of the crown ether may be substituted by —COOH, —CH$_2$OH, —C(O)N(CH$_3$)$_2$, or C$_1$–C$_4$ alkyl. Alternately, hydrogens on adjacent core carbons of the aza-crown ether may be substituted with R$^{31}$ and R$^{32}$ (see Structure A below) wherein R$^{31}$ and R$^{32}$ together are either —(CH$_2$)$_3$— or —(CH$_2$)$_4$— (see Structure B below, where R$^1$ and R$^2$ are part of an aliphatic system); or R$^1$ and R$^2$ together are —(CH)$_4$— (see Structure C below, where R$^{31}$ and R$^{32}$ are part of an aromatic system). Finally, hydrogens on core carbons on either side of core nitrogen or oxygen atom may be substituted with $R^{31}$ and $R^{32}$ wherein $R^{31}$ and $R^{32}$ together are —(CH)$_3$— such that a pyridinium or oxonium ring is incorporated into the aza-crown ether (see Structure D below). In the structures, L means

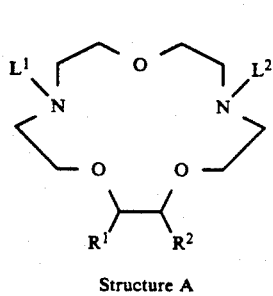

Structure A

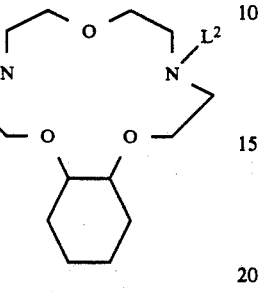

Structure B

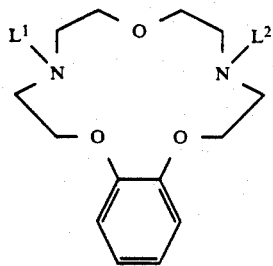

Structure C

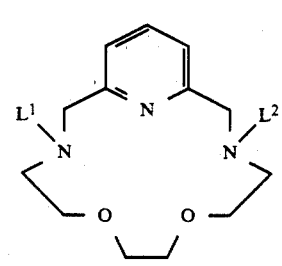

Structure D

In the compounds of the present invention, the crown ethers are preferably selected from the group consisting of: monoaza-12-crown-4, diaza-12-crown-4, monoaza-15-crown-5, diaza-15-crown-5, monoaza-18-crown-6 and diaza-18-crown-6. Especially preferred crown ethers are 1,7-diaza-4,10-dioxacyclododecane, 1,7-diaza-4,10,13-trioxacyclopentadecane and 1,10-diaza-4,7,13,16-tetraoxacyclooctadecane.

According to the invention, at least one of the ligand(s) that is attached to the aza-crown ether via the sp$^3$-hybridized core nitrogen(s) will be a heteroaromatic fluorophore that bears an additional cation chelating center. Heteroaromatic fluorophores bearing additional cation chelating centers that are used in the compounds of the present invention are shown below as Structure 1 and Structure 2 ligands. In addition, there may be one or more non-fluorophore moieties attached to the aza-crown ether. These non-fluorophore moieties are collectively referred to as "Structure 3 ligands."

In the compounds of the present invention, compounds that contain "Structure 1 ligands" will contain heteroaromatic fluorophores selected from the group of ligands shown in the Structure 1 general formula below:

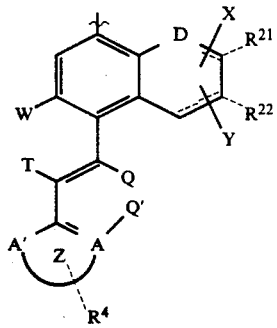

Structure 1 wherein,
A and A' are independently C, N, O or S;
D is N or O;
Q is H or NR$^1$R$^2$ where R$^1$ and R$^2$ are independently —H, lower alkyl (C$_1$–C$_4$), —CH$_2$COOH, —CH$_2$CH$_2$OH, or phenyl (—C$_6$H$_5$), or R$^1$ and R$^2$ together are —(CH$_2$)$_4$—, —(CH$_2$)$_5$—, or —CH$_2$CH$_2$OCH$_2$CH$_2$—;
Q' is H unless A is NR$^3$, O or S; or
Q and Q' together are NR$^3$, and A is C;
R$^3$ is selected from the group consisting of H, —CH$_3$, —C$_2$H$_5$ and —CH$_2$COOH;
R$^4$ is (E)$_n$ where n=0–3, and E is a polar electron-withdrawing function selected from the group consisting of —CO$_2$H, —CO$_2$R$^1$, —CONR$^1$R$^2$, —SO$_3$H, —SO$_2$NR$^1$R$^2$, —SO$_2$CF$_3$, —COCH$_3$, and —CN, where R$^1$ and R$^2$ are independently —H, lower alkyl (C$_1$–C$_4$), —CH$_2$COOH, —CH$_2$CH$_2$OH, or phenyl (—C$_6$H$_5$), or R$^1$ and R$^2$ together are —(CH$_2$)$_4$—, —(CH$_2$)$_5$—, or —CH$_2$CH$_2$OCH$_2$CH$_2$—;
R$^{21}$ is selected from the group consisting of —H, —CH$_3$, —C$_2$H$_5$, other lower alkyls up to C$_4$, —OCH$_3$, —COOH, C$_1$–C$_4$ alkoxy, and —OC(O)CH$_3$; or
R$^{21}$ and R$^{22}$ together are —CH=CH—CH=CH—, both X and Y are double bonds and D is N so that D, R$^{21}$, and R$^{22}$ form an acridine ring system;
W is H and T is H; or
W and T together are O or NR$^3$;
X is a double bond when D is N, and a single bond when D is O;
Y may be either a double or a single bond; and
Z is an aromatic or heteroaromatic system coupled to the 5-position of one 2-aminophenoxy ring through a trans ethylenic linkage, wherein said ethylenic linkage may itself be part of an aromatic heteroaromatic ring system, or
Z is an aromatic or heteroaromatic system coupled to the 5-position of a substituted benzene ring wherein said ethylenic linkage may likewise be part of an aromatic heteroaromatic ring system.

In the compounds of the present invention, compounds that contain "Structure 2 ligands" will contain heteroaromatic fluorophores selected from the group of ligands shown in the Structure 2 general formula below:

Structure 2

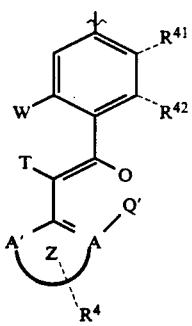

wherein,

A and A' are independently C, N, O or S;

Q is H or NR¹R² where R¹ and R² are independently —H, lower alkyl (C₁-C₄), —CH₂COOH, —CH₂CH₂OH, or phenyl (—C₆H₅), or R¹ and R² together are —(CH₂)₄—, —(CH₂)₅—, or —CH₂CH₂OCH₂CH₂—;

Q' is H unless A is NR³, O or S; or

Q and Q' together are NR³, and A is C;

R³ is selected from the group consisting of —H, —CH₃, —C₂H₅, and —CH₂COOH;

R⁴ is (E)$_n$ where n=0–3, and E is a polar electron-withdrawing function selected from the group consisting of —CO₂H, —CO₂R¹, —CONR¹R², —SO₃H, —SO₂NR¹R², —SO₂CF₃, —COCH₃, and —CN, where R¹ and R² are independently —H, lower alkyl (C₁-C₄), —CH₂COOH, —CH₂CH₂OH, or phenyl (—C₆H₅), or R¹ and R² together are —(CH₂)₄—, —(CH₂)₅—, or —CH₂CH₂OCH₂CH₂—;

R⁴¹ is selected from the group consisting of —OH, —OCH₃, —OCH₂COOH, —OCH₂CH₂OH, C₂-C₄ alkoxy, —NR¹⁴R¹⁵, —COOH, —C(O)NR¹⁴R¹⁵, or —OC(O)CH₃ where R¹⁴ and R¹⁵ are independently —H, lower alkyl (C₁-C₄), —CH₂COOH, —CH₂CH₂OH, or phenyl (—C₆H₅);

R⁴² is selected from the group consisting of —H, —CH₃ or —COOH;

W is H and T is H; or

W and T together are O or NR³; and

Z is an aromatic or heteroaromatic system coupled to the 5-position of one 2-aminophenoxy ring through a trans ethylenic linkage, wherein said ethylenic linkage may itself be part of an aromatic heteroaromatic ring system, or Z is an aromatic or heteroaromatic system coupled to the 5-position of a substituted benzene ring wherein said ethylenic linkage may likewise be part of an aromatic heteroaromatic ring system.

In the compounds of the present invention, compounds that contain "Structure 3 ligands" will contain non-fluorophore ligands selected from the group consisting of:

—CH₂C(O)NR¹R² where R¹ and R² are independently —H, lower alkyl (C₁-C₄), —CH₂COOH, —CH₂CH₂OH, or phenyl (—C₆H₅), or R¹ and R² together are —(CH₂)₄—, —(CH₂)₅—, —CH₃CH₂OCH₂CH₂— (to form a pyrrolidine, piperidine, or morpholine ring, respectively);

—CH₂COOH; -2-pyridylmethyl (shown below as structure 4);

-2-tetrahydrofuranylmethyl (shown below as structure 5);

—CH₂CH₂OR$^a$ where R$^a$ is —H, (C₁-C₄) alkyl, —CH₂COOH, —CH₂CH₂OH, or phenyl (—C₆H₅);

or -2,5-dialkoxyphenyl where the alkoxy substituent is C₁-C₄ alkoxy (shown below as structure 6).

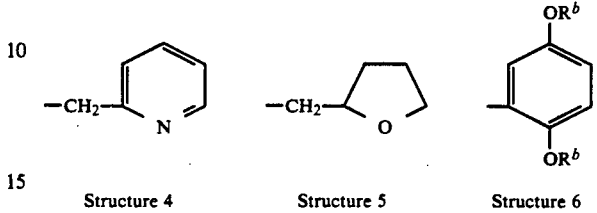

Structure 4    Structure 5    Structure 6

According to the invention, if a compound of the invention contains an aza-crown ether having at least two core nitrogens, the ligands (that are attached to the crown ether via sp³-hybridized core nitrogen(s)) can all be identical, or at least one ligand can be different from the other(s).

Finally, according to the invention, in the compounds of the invention, any of the carboxylates can be esterified with physiologically hydrolyzable esters, preferably acetoxymethyl esters.

DESCRIPTION OF SPECIFIC EMBODIMENTS

The synthetic routes to chelators of the present invention are shown schematically in FIG. 1 and described in detail in the section entitled COMPOUND SYNTHESIS. Additional details regarding the test equipment and procedures are given in the section entitled EXPERIMENTAL PROCEDURES.

Compound Design and Organic Synthesis

The new chelators of the present invention (which are comprised of (1) aza-crown ethers, whose core carbons may or may not be substituted with lower (C₁-C₄) alkyl, hydroxymethyl carboxy, carboxamido (including N-substituted) or saturated or unsaturated rings that are fused to the crown ring), wherein the crown ethers are linked via the core nitrogen(s) to (2) heteroaromatic fluorophores that bear additional cation liganding centers, begin with structure 1A. Structure 1A allows the initial combination of bare minimum of molecular parts, a macrocyclic ring of ligand groups with at least theoretically (17) the right size to favor Na⁺ over K⁺ binding, connected via an sp³-hybridized nitrogen to a rudimentary chromophore. The use of such aniline-type nitrogens to link chelating groups to chromophores has proved highly successful in the rational design of calcium indicators (16,18) and gives far larger spectral shifts than reliance on aryl ether oxygens (19).

Structure 1A was synthesized by Dix and Vögtle (3) but not characterized for cation binding properties. In the course of the present Work, the affinities of 1A for NA⁺ and K⁺ were found to be on the order of 0.5 and 0.2M⁻¹ in water, too weak to be characterized accurately. It was concluded that more donor groups were needed, especially out of the plane approximately defined by the macrocyclic ring.

Synthetic convenience suggested 1B, which was made by reacting 1-aza-4,7,10,13-tetraoxacyclopentadecane with 2-chloro-5-nitrobenzoic acid, followed by catalytic reduction of the nitro group to counteract its extreme electron-withdrawing power. Compound 1B had considerably higher Na+ affinity, 14M$^{-1}$, and Na+:K+ selectivity (13:1) than 1A, but its pK$_a$ was too high, 9.21.

Comparably high pK$_a$'s in other N,N-dialkylanthranilates are attributed to internal hydrogen bonding between zwitterionic amino and carboxylate groups (20). To eliminate such chelation of protons, the carboxylate was abandoned in favor of an sp$^3$-hybridized nitrogen in 1C, in which the two nitrogens are too far apart to engage the same proton at once. Chelator 1C was prepared by reaction of 1-aza-4,7,10,13-tetraoxacyclopentadecane with 8-tosyloxy-5-nitroquinoline followed by reduction of the nitro group. The resulting primary amino group was acetylated to block a tendency to auto-oxidize. Despite the replacement of the carboxylate of 1B by an uncharged ligand group in 1C, the Na+ affinity, 15M$^{-1}$, was not diminished. As desired, the pK$_a$ was lowered below 7.

Since addition of one additional donor group out of the main ring plane increased the Na+ affinity by more than an order of magnitude, a second donor group was added, as shown in structure 2CC. Molecular models suggested that this complex could neatly fold up around a sodium cation with the macrocyclic ring, forming an equatorial belt with the two additional donor groups capping the north and south poles. Chelator 2CC was prepared from the commercially available 1,7-diaza-4,10,13-trioxacyclopentadecane with 8-tosyloxy-5-nitroquinoline, followed by reduction and acetylation. Compound 2CC indeed had a greatly increased Na+ affinity, 190-415M$^{-1}$ depending on ionic strength. Fortunately, the K+ affinity did not increase to the same extent. Since the spectral change associated with K+ binding was only half that caused by Na+ binding, K+ probably could interact with only one of the two quinoline rings, presumably because K+ was too big to fit fully inside the macrocyclic ring but rather had to stay on one side of it. Compound 2CC was found, however, to have a major drawback in its excessive affinity for Mg$_{2+}$; nearly $1.3 \times 10^4$M$^{-1}$, which would give overwhelming interference from the typical value of 1 nM free intracellular Mg$^{2+}$. This Mg$^{2+}$-binding is unusual in its kinetic sluggishness, with association and dissociation rate constants of only 1.48M$^{-1}$s$^{-1}$ and $1.28 \times 10^{-4}$ s$^{-1}$ at 25 degrees, easily observable in a spectrophotometer without rapid mixing equipment. A reasonable explanation for the high affinity of Mg$^{2+}$ for 2CC is that the binding site can readily collapse compactly to fit the small Mg$^{2+}$ ion. As confirmation of this hypothesis, 2CC proved to have an affinity for Li+ comparable to that for Na+.

To prevent such compaction of the binding site, methyl groups were added to the quinoline 2-positions to act as buttresses to prevent the quinoline nitrogens from too closely approaching the plane of the macrocyclic ring. The resulting chelator, 2DD, had <10$^{-4}$ the Mg$^{2+}$ affinity, and <10$^{-2}$ the Li+ affinity of 2CC, yet retained more than half the Na+ affinity. Since the two methyl substituents did not affect the Na+:K+ selectivity, they clearly made a major improvement overall. Nevertheless, though 2DD had highly satisfactory ionic selectivities for Na+ over the other alkali and alkaline earth metals, it proved to lack the further properties necessary to make it biologically useful as a fluorescent indicator. Its fluorescence quantum yield was only 0.01, probably inadequate for use as a fluorescent intracellular indicator, considering its need for UV excitation and its modest extinction coefficients. Its proton affinity was undesirably high, the pK$_a$ for the 1st proton being 7.55. Of course, it had no carboxylates to enforce water solubility and retention inside cells.

In the hope of increasing the fluorescence quantum efficiency, several analogues of 2DD were synthesized with 6-alkoxy substituents on the quinaldines instead of the 5-acetamido groups. The rationale was that 6-methoxyquinolinium fluorophores are responsible for the strong fluorescence of quinine. Also, addition of a 6-methoxy substituent did turn a weakly-fluorescing Ca$^{2+}$ indicator, quin-1, into a considerably stronger fluorescent dye, quin-2. (See U.S. Pat. No. 4,689,432.) The vacancy of the 5-position would permit attachment of more extensive conjugation to extend the wavelengths of excitation and emission. However, an entirely different synthetic strategy was needed since the 5-position could not readily bear the nitro group needed to activate aromatic nucleophilic substitution. For this reason the crown macrocycle was synthesized from scratch by reaction of 6-methoxy-8-aminoquinaldine (21) with 3,6-dioxaoctanedioyl chloride (22), reduction of the diamide with diborane, re-acylation of the diamine with diglycolic acid chloride, then aluminum hydride (23) reduction of the amide. Aluminum hydride was found to give better results than diborane, since the latter gave products from which it was difficult to remove boron fully. The re-acylation with diglycolic acid chloride was run under high dilution conditions to favor macrocycle closure over polymer formation. Conventionally (22), triethylamine is added to neutralize the HCl generated during acylation, but this base itself slowly destroyed the acid chloride, presumably through ketene intermediates. When the amine to be acylated is reactive, this side reaction is not serious, but with a bulky and less nucleophilic aromatic diamine such as 1,8-bis(2-methyl-6-methoxy-8-quinolinylamino)-3,6-dioxaoctane, a weaker tertiary base such as N,N-dimethylaniline is preferable to triethylamine.

First trials of 6-substituted quinolines were conducted on the 6-hydroxyquinaldine 2FF obtained by demethylation of the precursor 2EE bearing methoxyls. Compound 2FF, however, proved to have yet another disappointment in its quantum efficiency; about 0.01 and 0.005, with and without Na+, respectively. Therefore, 2EE was formylated at the 5-position, demethylated, and coupled with dimethyl 4-bromomethyl phthalate (24) to form the quinolinofuran 2GG. The Na+ affinity of 2GG was even higher than that of 2DD, perhaps aided by some long-range electrostatic attraction of the cation to the four negative charges. Unfortunately, the proton affinity likewise rose to a pK$_a$ of 7.9. Since the quantum efficiencies were the same low values as those of 2FF, this approach had to be abandoned.

In order to bring about the hoped-for increase in both the wavelength and quantum efficiency of fluorescence, a shift was made from quinoline nuclei to acridines as in 2HH and 2II. These compounds were prepared from 4-methoxy-9-acridone by reduction to the acridine (25), nitration at the 1-position, replacement of the methoxy group by hydroxy, tosylation, reaction with 1,7-diaza-4,10,13-trioxacyclopentadecane, finishing with reductive acylation. The acetamido derivative 2HH analogous to 2CC and 2DD proved insufficiently soluble in water for spectrophotometry, so the more hydrophilic hemisuccinamide 2II was prepared. This had the highest Na affinity (3125M$^{-1}$) and Na+:K+ selectivity (>500) yet obtained. Unfortunately, the pK$_a$, 8.19, was also nearly a record. Though the absorbance band was indeed shifted into the visible, the fluorescence quantum yield remained very poor, so that the acridine nucleus was only accentuating the undesirable features of 2DD.

The excessively high $pK_a$'s of the quinaldines and acridines seemed attributable to protonation on the heterocyclic rather than the amino nitrogens, because protonation gave rise to bathochromic shifts whereas metal cations were hypsochromic. One way to eliminate the high $pK_a$ is to replace the heterocyclic nitrogens by less basic donor atoms such as ether oxygens. The first attempt at such a molecule was 2JJ, prepared by reaction of the diaza crown with 2-fluoro-5-nitroanisole (26), followed by reduction and acetylation as usual. 2JJ indeed had the highest $pK_a$ at 6.31, much lower than the $pK_a$'s for the quinaldines and acridines. Also, protonation of 2JJ gave a hypsochromic shift very similar to metal cation binding, confirming that the site of protonation had shifted to an amino nitrogen. Despite the decreased donor strength of oxygens compared to nitrogens, Na+ affinity was still respectable, 83$M^{-1}$ at I=0.15. However, 2JJ absorbed only in the deep UV, as expected from the small size of its chromophore.

A useful fluorescent indicator would require a chromophore with a much longer conjugation path. The normal site of attachment of such conjugation would be para to the dialkylamino group, but that position is occupied by a nitrogen. All common substituents that extend conjugation through a —N=0 are significantly electron-withdrawing, so they would depress the Na+ affinity strongly.

To escape this quandary, an electrophile other than a nitrohalobenzene was needed that would react with amines and then be reducible to an electron-donor-substituted aromatic ring. An attractive electrophile was p-benzoquinone. By reaction (27,28) of a large excess of this cheap reagent with the diaza crown, it was possible to produce 2KK in which each quinone bears only one amino substituent. Reduction and alkylation gave aminoquinol ether 2LL. Vilsmeier formylation of 2LL followed by regioselective demethylation (29) of the phenol ortho to the formyl gave salicylaldehyde 2MM. From this intermediate, various benzofurans can be prepared, all representing styryl fluorophores with cis-trans isomerism prevented by heterocyclic ring formation. Thus 2MM reacted with 2 moles of dimethyl 4-bromomethylphthalate to form the tetramethyl ester of the benzofuran phthalate 2NN. Alternatively, 2MM with ethyl 2-chloromethyloxazole-5-carboxylate gives the ester of benzofuran oxazole 2OO, a relative of the successful fluorescent $Ca_{2+}$ indicator fura-2. (See U.S. Pat. No. 4,603,209.) Finally, when 2NN and 2OO proved difficult to load as acetoxymethyl esters, 2PP was synthesized from 2MM plus 2 moles of dimethyl 4-bromomethylisophthalate. For convenience we refer to 2NN, 2OO, and 2PP as "SBFP", "SBFO", and "SBFI" respectively, short for sodium-binding benzofuran phthalate, oxazole, or isophthalate.

The most successful compounds of the present invention synthesized and tested so far are N-substituted derivatives of commercially available 1,7-diaza-4,10,13-trioxacyclopentadecane. This crown ether (also trivially known as "diaza[15]-crown-5", "diaza-15-crown-5" or "Kryptofix 21") was chosen initially because it forms a "belt" of about the right size to fit equatorially around a Na+ cation (17). To make indicators for Li+ or K+ one would choose the next smaller or next larger crown ethers, 1,7-diaza-4,10-dioxacyclododecane or 1,10-diaza-4,7,13,16-tetraoxacyclooctadecane, respectively. The latter did indeed confer K+ selectivity, as shown by compounds 3JJ and 3NN.

Methods for synthesizing crowns with substituents on the carbons of the macrocyclic ring, or rings fused to the macrocycle, have been reviewed by Weber & Vögtle (1976), Laidler & Stoddart (1980) and Nakatsuji, et al. (1983). (See refs. 48-50, respectively.) Such methods can be used by those skilled in the art, without undue experimentation, to make crowns with substituents on the carbons of the macrocyclic ring, and rings fused to the macrocycle. By way of example, reaction of the bis(dimethylamide) of tartaric acid or of a dialkyl ester of tartaric acid with ethyleneimine or a N-protected derivative thereof would give an analogue of 1,8-diamino-3,6-dioxaoctane bearing ester or amide substituents on the 4 and 5 positions. (Instead of an ethyleneimine derivative, N-(2-bromoethyl)phthalimide could also be used, followed by removal of the phthalimide protecting groups using hydrazine.) This diamine would be condensed with diethyleneglycol ditosylate or a bis(2-haloethyl)ether to form a 1,7-diaza-15-crown-5 with carboxamide or ester substituents at the 11- and 12-positions of the macrocycle. Alternatively, condensation of the diamine with triethyleneglycol ditosylate or bis(2-haloethoxy)ethane would give a 1,10-diaza-18-crown-6 with carboxamide or ester substituents at the 5- and 6-positions of the macrocycle. If hydroxymethyl substituents were desired, they could be obtained by metal hydride reduction of the ester substituents. These crown building blocks would replace Kryptofix 21 (1,7-diaza-4,10,13-cyclopentadecane) and Kryptofix 22 (1,10-diaza-4,7,13,16-tetraoxacyclooctadecane) in the syntheses described above for fluorescent indicators. Upon the final mild basic hydrolysis of ester functions, any carboxamide or hydroxymethyl groups would be expected to survive unchanged, whereas any remaining ester groups derived from tartaric acid would be hydrolyzed to carboxylate groups.

Similarly, if 2,3-butanediol were used at the outset instead of a tartaric acid derivative, the result would be the addition of a pair of vicinal methyl substituents to the 11- and 12- positions of the 1,7-diaza-4,10,13-cyclopentadecane ring or the 5- and 6-positions of the 1,10-diaza-4,7,13,16-tetraoxacyclooctadecane ring. Use of catechol, 1,2-cyclohexanediol or 1,2-cyclopentanediol instead of 2,3-butanediol would eventually generate crown ethers with benzene, cyclohexane or cyclopentane rings fused to the 11- and 12-positions of the 1,7-diaza-4,10,13-cyclopentadecane ring or to the 5- and 6-positions of the 1,10-diaza-4,7,10,13-tetraoxacyclooctadecane ring.

Yet another standard permutation of the crown ether system consists of replacing one or more of the oxygen donor atoms by the nitrogen of a pyridine ring. For example, an obvious analog of 1,7-diaza-4,10,13-trioxacyclopentadecane is 5,8-dioxa-2,11-diaza[12]-(2,6)-pyridinophane, prepared either by diborane or lithium aluminum hydride reduction of 5,8-dioxa-2,11-diaza[12](2,6)-pyridinophane-1,12-dione, or by removal of tosyl groups from 2,11-ditosyl-5,8-dioxa-2,11-diaza[12](2,6)pyridinophane (see Reaction Scheme 1, below; also see ref. 48). The resulting pyridinophane could be used in place of 1,7-diaza-4,10,13-trioxacyclopentadecane in all the syntheses of fluorescent indicators described above.

Reaction Scheme 1

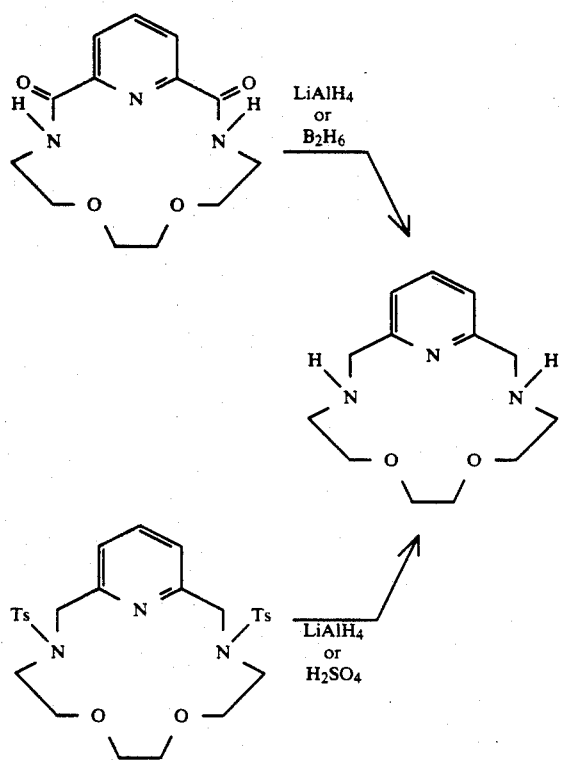

Reaction Scheme 2

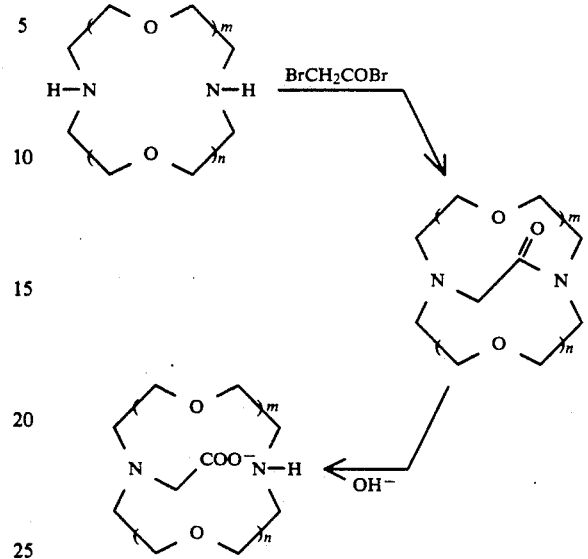

In order to prepare indicators with two different substituents attached to the nitrogens of the diaza crown ring, the most general strategy is to acylate the parent diaza crown with one equivalent of a standard protecting reagent such as acetic anhydride, trifluoroacetic anhydride, ethyl chloroformate, or benzyl chloroformate. A mixture of unreacted crown, monoamide, and diamide will form, from which the monoamide should be separable by chromatography. Both the unreacted crown and the diamide can be recycled, the latter by complete or partial deprotection. Once the monoprotected diaza crown is available, the first liganding side arm or fluorophore can be attached to the single free nitrogen in precise analogy to the reactions of 1-aza-4,7,10,13-tetraoxacyclopentadecane described above. The protecting group can then be removed by standard means to allow the second liganding side arm or fluorophore to be attached to the newly freed remaining nitrogen of the diaza crown. Of course, the use of the amine protecting groups might be bypassed by directly reacting the parent diaza crown with a limited quantity of an electrophile such as a nitrohalobenzene or benzoquinone, then separating the desired mono-substitution product from unreacted crown and di-substitution products. However, the di-substitution product would not be recyclable. In the particular case that one ligand group is a —$CH_2COO^-$ or an ester or amide derived therefrom, a useful approach is to react the parent diaza crown with one equivalent of bromoacetyl bromide, $BrCH_2COBr$, under high-dilution conditions. This reaction is shown below as Reaction Scheme 2:

Upon hydrolysis of the amide bond, one nitrogen would be freed to allow attachment of a fluorophore by the usual reactions already described above.

The diaza crowns that do not have liganding substituents attached to the main crown ring actually have very poor cation affinities and selectivities (36) and of course lack any optical properties. Several workers have previously tried adding one liganding substituent above the plane formed by the main crown ring (37-39). Such structures, dubbed "lariats" for their shape, can have modestly improved Na+ affinities. Some "lariats" can extract alkali and alkaline-earth cations into 1,2-dichloroethane from aqueous medium at high pH (38,39). However, selectivities for Na+ over K+ are poor, <1 log unit, and none has been shown to respond optically to Na+ in a purely aqueous medium. Our initial trials of crowns with one axial substituent (1A-1C) confirmed their inadequate Na+ affinity and axial substitutents to two aromatic ether or $sp^2$ nitrogen ligand groups, adequate to very good selectivity and affinity for Na+ resulted. The highest Na+ affinities and selectivities over K+ were obtained with quinoline or acridine ring nitrogens as the axial donors, but despite many permutations, all such chelators suffered from inadequate proton rejection and low fluorescence quantum efficiencies. The latter properties were greatly improved by changing the axial donors to aromatic ether oxygens. Upon extension of the aromatic rings to form suitable fluorophores, Na+ indicators SBFP, SBFI and SBFO were obtained with properties suitable for biological application. SBFP and SBFI have somewhat better Na+ affinity and selectivity than SBFO, but SBFO has somewhat longer wavelengths of excitation and higher quantum efficiency of fluorescence. SBFI is our currently preferred indicator because (1) it is the most easily loaded into cells by hydrolysis of its acetoxymethyl ester, (2) its excitation and emission wavelengths are slightly longer than SBFP, (3) its ionic selectivities are slightly better than SBFP, and (4) the brightness of its fluorescence seems adequate.

In retrospect, the Na+ to K+ selectivities (20 to 500) and Na+ to divalent cation selectivities (>1) of 2CC-2NN are unexpectedly good compared to recently reported results with other derivatives of diaza[15]-crown-5 (40–43). Addition of carboxymethyl groups to both nitrogens gives a chelator dianion (40,41) with a strong preference for divalent and trivalent metals over $Na^+$. Gokel and coworkers (42,43) have synthesized several "bibracchial lariat ether" derivatives of diaza[15]-crown-5. These "BiBLEs" have liganding sidearms on each nitrogen, linked through flexible aliphatic linkages rather than rigid aromatic rings. They show $Na^+/K^+$ selectivities of only 1.0 to 4.9 even though they were measured (43) in anhydrous methanol, a solvent known to foster much higher absolute affinities and selectivities (17) than the aqueous salt solutions in which biologists must work. The improved selectivities of the present compounds may at least partly arise from the rigidity of our pendant aromatic groups, which force the crown nitrogen and the pendant ligand —OMe or —N= into a cis conformation ready to make the desired five-membered chelate ring with the $Na^+$ ion. Indeed, the bulkier and more rigid the heteroaromatic ligand, the higher the observed $Na^+/K^+$ selectivity (compare 2JJ, 2DD, and 2II).

Though SBFI is at the low end of the selectivity range, it remains useful inside cells for two reasons. Firstly, $Na^+$ binding affects its spectra more strongly than does $K^+$ binding, so that replacement of a bound $K^+$ by a $Na^+$ is spectroscopically visible. Secondly, under most circumstances cellular $Na^+$ and $K^+$ are not free to vary independently but are constrained by osmotic balance and electroneutrality to have a constant sum which is approximately known (31,44). Under these conditions, $[Na^+]_i$ can be calibrated even when it is $<10\%$ of $[K^+]_i$. The main effect of the imperfect selectivity is to compress the dynamic range of the fluorescence signal. Calibration and interpretation would become more problematic if the cells were subjected to drastic changes of osmolarity or ionic substitutions.

Higher $Na^+$ affinities and selectivities are known to be attainable in cryptands (5,22) and spherands (8,9), chelators whose metal binding sites are more rigidly defined in three dimensions than those of the modified crown ethers exploited in this work. The choice was made, originally, to avoid these more elaborate structural types mainly because the conformational rigidity and preorganization of their cavity would tend to reduce the spectroscopic shift upon metal binding. The large spectral shifts obtained with our crown ethers are analogous to protonation of the aromatic amino groups or to $Ca_{2+}$ binding to tetracarboxylate indicators like fura-2. Such shifts are consistent with a mechanism in which cation binding causes a major loss of conjugation between the amino groups and the rest of the chromophore, at least partly by twisting the $>N-Ar$ bond (13,16,18).

Molecular models of analogous cryptands suggested to us that the $>N-Ar$ bond would start mostly twisted even before metal binding. Indeed, in one cryptand indicator of $Na^+$, the spectral shifts were modest, at most 30% change in intensity at any wavelength (6). However, a more recent cryptand has been shown (7) to give a large emission shift upon $Na^+$ binding, a finding that suggests that in the excited state there is more $>N-Ar$ conjugation for $Na^+$ to disrupt. Spherands are even larger, more hydrophobic, and more rigid. The main mechanism by which they can give optical shifts upon metal binding is by ejection of a proton from the cavity (9), but this mechanism inherently must be pH-sensitive, an unwanted feature. The three-dimensional rigidity of both cryptands and spherands also tends to slow the kinetics of association and dissociation of cations; dissociation time constants of seconds to days often result (45). Finally, it should be noted that excessive $Na^+$ affinity (9) would actually be undesirable in an indicator intended to signal free $[Na^+]$ concentrations without perturbing them. Instead, the dissociation constant should ideally be at the middle of the range of physiological concentrations of interest, therefore in the 5–20 mM range as actually achieved in SBFP and SBFI.

Spectral and Cation-Binding Properties

SBFI has extinction coefficients of 42,000–47,000, as expected for molecules containing two styryl chromophores. Its fluorescence quantum efficiency is respectable, 0.08 and 0.045 with and without $Na^+$. Both the $Na^+$ affinity and $K^+$ affinities, $166 M^{-1}$ and $7 M^{-1}$, are a little stronger than those of the model compound 2JJ. Some or all of this increment may just be the electrostatic attraction of the four remote carboxylates for cations. However, the highest $pK_a$, 6.1, is still low enough so that most physiological pH variations will have little effect on the dye spectra or effective $Na^+$ affinity. To enable physiochemical comparison with earlier chelators, the above affinities were measured against truly inert background cations such as tetramethylammonium or $Cs^+$, at a pH high enough for protonation to be completely negligible. Biologically more relevant values are obtained in $Na^+-K^+$ mixtures. When the sum of the two cations is held constant at 135 mM, with 1 mM $Mg^{2+}$ present at pH 7.05 as would be reasonable for vertebrate cytoplasm, the apparent dissociation constant for $Na^+$ is 17–19 mM, as may be seen in FIG. 2A. $Na^+$ binding shifts both the excitation and emission spectra to shorter wavelengths. Though $Na^+$ shifts the excitation peak wavelength only 8 nm from 344 to 336 nm, it also makes the long-wavelength side of the excitation spectra roll off much more steeply. The ratios of excitation efficiencies at 335–340 to that at 375–380 nm therefore undergoes a large increase with $Na^+$ binding. This sort of spectral shift is roughly similar to the way fura-2 responds to $Ca_{2+}$, except that SBFP and SBFI are excited at slightly shorter wavelengths and do not change their ratio quite as much as fura-2 does (13). The emission spectra of SBFP and SBFI (FIG. 3) shift very little as $Na^+$ replaces $K^+$, so that these dyes are like fura-2 in being most sensitive in excitation ratioing rather than emission ratioing (13).

Selectivities of SBFP and SBFI against other cations are also adequate (Table I). In the presence of 13.5 mM $Na^+$ and 121.5 mM $K^+$, the highest apparent $pK_a$ of SBFI is 6.09. Moreover, acidification depresses the 335–340 nm and the 375–380 nm excitation amplitudes about equally (FIG. 4), so that the ratio does not change significantly. Ratioing therefore not only normalizes for amount of dye in the optical path but also improves the discrimination against pH changes. $Li^+$ binding causes a greater shift of the SBFI excitation peak to shorter wavelengths but a lesser increase in amplitude than $Na^+$ binding does; the $Li^+$ affinity, $15 M^{-1}$ ($K_d$ 67 mM), is also weaker than the $Na^+$ affinity. Dissociation constants for $Mg^{2+}$ and $Ca^{2+}$ are high enough (about 60 mM and 38 mM respectively) for cytosolic levels of those ions to have insignificant effect. Curiously, $Ca^{2+}$ is unique in causing a large hypsochromic shift of the emission peak, to 432 nm. All the above-mentioned salts except tetramethylammonium seem to cause a slight non-specific quenching of SBFI at very high concentrations. For example, CsCl causes no spectral shift at all, but 100, 200, and 500 mM CsCl depress the fluorescence by 9, 14, and 21% from the metal-free level. This effect is not a heavy-atom effect of Cs, since large excesses of Li$^+$, Na$^+$, and K$^+$ also slightly quench their SBFI complexes. It may represent weak quenching by Cl$^-$, since acetate and fluoride gave much less of the effect.

Compared with SBFP and SBFI, SBFO has even higher quantum efficiencies of fluorescence, 0.44 and 0.14 with and without Na$^+$. Because the oxazole group in SBFO is more electron withdrawing than the phthalate in SBFP, SBFO has somewhat longer wavelengths of excitation and emission as well as a reduced affinity for Na$^+$, 20M$^{-1}$. This 50 mM dissociation constant with tetramethylammonium as background ion rises to 95 mM when measured against a K$^+$ background with [Na$^+$]+[K$^+$]=135 mM (FIG. 5). Again, Na$^+$ binding causes a large change in the ratio of excitation efficiencies at 340–350 nm to 380–390 nm, rather like the effect of Ca$^{2+}$ on the related fura-2. Competition from protons is also reduced, with a highest pK$_a$ of only 5.34.

To check the basis for the Na$^+$ selectivity of the above indicators, we synthesized 3JJ-3NN, analogs of 2JJ-2NN but with six heteroatoms in an 18-membered ring instead of the usual five heteroatoms in a 15-membered ring. As expected, the increased cavity size made K$^+$ the preferred cation, though by only a small margin over Na$^+$ (Table I). 3NN is named "PBFP" for potassium-binding benzofuran phthlate. Its excitation spectra are shown in FIG. 6 under the usual conditions of [Na$^+$]+[K$^+$]=135 mM. Now it is increasing K$^+$ or decreasing Na$^+$ that enhances the fluorescence at 340 nm excitation. The apparent K$_d$ for K$^+$ is 70 mM. Curiously, K$^+$ increases the intensity without much change in wavelength, so that PBFP works best at a single wavelength rather than in dual-wavelength ratio mode. Though its K$^+$:Na$^+$ selectivity is small, it may find some use for intracellular (though not extracellular) measurements because [K$^+$]$_i$ usually far exceeds [Na$^+$]$_i$.

TABLE 1

| Structure[a] | Dissociation constants[b] ($K_d$) in mM for | | | | | $pK_a$[c] | $K_d$ for Na+ in K+ at pH 7.0[d] | $pK_a$ in 14 mM Na+ 126 mM K+, 1 mM Mg2+[e] | Absorbance maxima[f] | | Emission maxima[f] | | Quantum efficiency[g] | |
|---|---|---|---|---|---|---|---|---|---|---|---|---|---|---|
| | Na+ | K+ | Mg2+ | Ca2+ | Li+ | | | | −Na+ | +Na+ | −Na+ | +Na+ | −Na+ | +Na+ |
| 1A | | | | | | | | | 252 (14.2) | 249 (8.7) | | | | |
| 1B | 71 | ~900 | | | | 9.21 | | | 295 (shoulder 1.1) | 296 (1.1) | | | | |
| 1C | 67 | ~1000 | 12 | 10 | 63 | 6.32 | | | 349 (2.4) | 304 (2.6) | | | | |
| 2CC | 5.3, 2.4[h] | 225[g] | .078[i] | .075 | 2.8 | 6.85, 5.43 | | | 252 (9.2) | 229 (13) | | | | |
| | | | | | | | | | 346 (4.7) | 304 (5.0) | | | | |
| 2DD | 9.4, 4.4[h] | 470 | >500 | 200−250 | 500 | 7.55, 5.62 | | | 250 (19) | 230 (23) | | | | |
| | | | | | | | | | 344 (4.9) | 306 (6.0) | 525 | 510 | .01 | .01 |
| 2FF | 8.9 | | | | | | | | 256 (22) | 237 (24) | 497 | 466 | .0035 | .0040 |
| 2GG (SQFP) | 4.7 | | | | | 7.9, 6.8 | ~300 | | 363 (2.4) | 362 (2.3) | 485 | 525 | .005 | .01 |
| | | | | | | | | | 373 (24) | 362 (31) | | | | |
| 2II | 0.32, 0.4[h] | 178, 110[h] | | j | 11.5 | 8.19, 6.86 | | | 308 (22) | 307 (28) | | | | |
| | | | | | | | | | 414 (4.2) | 360 (6.1) | 480 | 625 | <.001 | <.001 |
| | | | | | | | | | 359 (4.1) | | | | | |
| 2JJ | 12 | 290 | >100 | >100 | 72 | 6.31, 5.0 | 30 | | 244 (48) | 251 (48) | | | | |
| | | | | | | | | | 261 (10.8) | 280 (5.4) | | | | |
| 2LL | 10−20 | | | | | | | | | 249 (10.7) | | | | |
| | | | | | | | | | 295 (4) | 291 (4) | | | | |
| | | | | | | | | | 213 (13) | | | | | |
| 2NN (SBFP) | 8.5 | 161 | 18 | 40 | 347 | 6.3, 5.5 | 19 | 6.4, 5.6 | 342 (45.5) | 334 (51.6) | 528 | 505 | .036 | .091 |
| 2OO (SBFO) | 50, 22[h] | 170[h] | 63 | 38 | 68 | 5.34, 4.15 | 95 | 4.82, 4.03 | 355 (25) | 343 (27) | 515 | 500 | .14 | .44 |
| 2PP (SBFI) | 7.4 | 166 | 60 | | | 5.89, 5.19 | 17−18[k] | 6.09, 5.1 | 346 (42) | 334 (47) | 551 | 525 | .045 | .083 |
| | | | | | | | | 6.06, 5.26 | | | | | | |
| 3JJ | 20 | 10 | | | | | | | 258 (3.5) | 281 (2.0)[l] | | | | |
| | | | | | | | | | | 249 (3.4)[l] | | | | |
| 3NN (PBFP) | 260 | 83 | 40 | 16 | 380 | | 70[m] | 6.68 | 344 (23) | 337 (25)[l] | 518 | 494[l] | .0075 | .12[l] |
| 3PP (PBFI) | 21 | 8 | | | | | 100[m] | 5.78, 5.17 | 350 (42) | 344 (42)[l] | 545 | 504[l] | .024 | .072[l] |

TABLE 1 FOOTNOTES

Footnote [a]: For molecular structures, see FIG. 1.

Footnote [b]: Except where otherwise noted, these dissociation constants were measured with the chelator dissolved in 0.1 M tetramethylammonium chloride, at a pH held high enough with 1−5 mM tris(hydroxymethyl)aminomethane for protonation to be insignificant. The absorbance spectrum, or the fluorescence excitation spectrum for those compounds (2GG, 2NN, 2OO, 2PP, 3NN) with acronyms was measured as a function of the concentration of cation added as a solid or concentrated aqueous solution of the halide salt. No correction has been made for the changing ionic strength of the solution, which started from 0.1 M and increased, but the absorbances and fluorescence amplitudes were applied for dilution of the dye and any slight quenching due to high concentrations of Cl−.

Footnote [c]: These protonation constants were determined in 0.1 M tetramethylammonium chloride, 10 mM tris(hydroxymethyl)aminomethane, titrated with 5 M H₃PO₄ to successively lower pH values measured with a Radiometer PHM84 meter. Other details resembled the metal titrations above.

Footnote [d]: These dissociation constants are effective values for Na+ against a K+ background such that [Na+] + [K+] = 135 mM, at pH 7.05 buffered with 10 mM N-(morpholino)propanesulfonic acid. They were measured by spectrofluorometry (or spectrophotometry for 2JJ) as shown in FIGS. 2 and 5, and are in units of millimolar.

Footnote [e]: These protonation constants are for dye in 126 mM KCl, 14 mM NaCl, 1 mM MgCl₂, 4 mM tetramethylammonium chloride, titrated with 5 M H₃PO₄ as in FIG. 4.

Footnote [f]: Absorbance maxima refer to the main peaks, measured in 100 mM tetramethylammonium chloride plus 1−5 mM tris(hydroxymethyl)aminomethane (−Na+), or with enough NaCl added (0.2−1 M) to saturate the Na+ binding (+Na+). The first number is the wavelength in nanometers, followed in parentheses by 10⁻³ × the corresponding extinction coefficient, M⁻¹cm⁻¹. Extinction coefficients for most of the compounds are lower limits because most of the chelators were obtained by chromatographic purification as gums or oils, which revealed no other significant absorbing species but may have included traces of chromatographic solvents or other non-absorbing impurities. Emission maxima in nanometers and quantum efficiencies were measured in the same solutions as used for absorbance ±Na. Emission maxima are not corrected for the spectral sensitivity of the emission detection. Quantum efficiencies were measured (13) by comparing the integral of the corrected emission spectrum with the corresponding integral for a solution of quinine bisulfate in 1 N H₂SO₄ of matched absorbance at the excitation wavelength. Quinine was assumed to have a quantum efficiency of 0.55.

Footnote [h]: These dissociation constants were measured at 3.0 M ionic strength by mixing solutions of dye in 3.0 M NaCl with the same dye concentration in 3.0 M tetramethylammonium chloride.

Footnote [i]: Free [Mg2+] was controlled by Mg2+-nitrilotriacetate buffers at pH 8.5.

Footnote [j]: At several mM concentrations of Mg2+ or Ca2+, precipitate began to form, so dissociation constants could not be quantified.

Footnote [k]: An effective $K_d$ of 28 mM was additionally determined for SBFI-Na+ when [Na+] + [K+] = 280 mM as might be more appropriate for the cytoplasm of marine organisms.

Footnote [l]: These values for the K+ selective chelators 3JJ and 3NN refer to spectra in saturating K+ rather than Na+.

Footnote [m]: Effective $K_d$ in millimolar for K+ against a Na+ background, where [Na+] + [K+] = 135 mM, as measured in FIG. 6.

EXPERIMENTAL PROCEDURES

UV absorbance spectra were recorded initially on a Cary 210 and later on a Perkin-Elmer Lambda Array 3840 spectrophotometer. Fluorescence excitation and emission spectra and quantum efficiencies were measured on a Spex Fluorolog 111 as described previously (13).

Proton dissociation constants of the chelators were measured by spectrophotometry or spectrofluorometry of buffered solutions, containing either 100 mM tetramethylammonium chloride as inert supporting electrolyte, or 121.5 mM $K^+$, 13.5 mM $Na^+$, and 1 mM $Mg^{2+}$ to simulate the cation environment of vertebrate cytoplasm (14). Traces of UV-absorbing impurities in the tetramethylammonium chloride (Alfa Inorganics) were removed by filtration through acid-washed activated charcoal. The concentration of the tetramethylammonium chloride was then measured by chloride titration, and the absence of significant Na contamination was verified with a sodium-selective glass electrode (Microelectrodes Inc.). When the chelators contained two protonatable nitrogens, the curve of absorbance or fluorescence versus pH was analyzed by computerized least-squares fitting to the equations for two arbitrary proton equilibria (15), with the added assumption that the two protonations each caused the same change in extinction coefficient or fluorescence. This assumption was based on the presence of two identical chromophores in each chelator and produced good fits to the experimental data.

Affinities for other cations were usually measured by titrating aqueous solutions of the indicator with metal chlorides added either as solid or from concentrated stock solutions, taking care to minimize dilution and correct for it. A convenient way to mass-produce premeasured micromole to millimole aliquots of solid NaCl or KCl was to pipet saline solutions into polypropylene micro test tubes and evaporate the water in an oven. The standard ionic background was again 100 mM tetramethylammonium chloride, usually with a few mM of tris(hydroxymethyl)-aminomethane base to hold the pH high enough (pH 8-9) to insure that protonation was negligible. This convenient titration procedure had the slight disadvantage that the ionic strength was not constant, especially when large quantities of a salt had to be added due to weak affinities. However, even drastic alterations in ionic strengths were found to have relatively little effect on apparent dissociation constants (Table I), as expected for monovalent cations binding to uncharged chelator sites. When constant ionic strength was desired, the chelator was made up at identical concentrations in matched solutions of NaCl, KCl, or tetramethylammonium chloride, then these stocks were mixed in the desired proportions. All measurements were made at room temperature (22°, ±2° C.).

COMPOUND SYNTHESIS

Proton NMR spectra were recorded on a Varian Instruments EM-390 at 90 MHz and on a 200 MHz Fourier-transform instrument (UCB-200) constructed in the Department of Chemistry, University of California, Berkeley. Peaks are reported below in the following format: NMR (solvent, operating frequency): chemical shift δ in ppm downfield from tetramethylsilane, multiplicity (s=singlet, d=doublet, dd=doublet of doublets, t=triplet, q=quartet, m=multiplet, br=broad), spin-spin coupling constant if appropriate, integrated number of protons; sometimes several adjacent peaks are too close for their integrals to be separated, in which case only the total integral for a cluster is stated. Column chromatography, reverse-phase thin layer chromatography, and preparative layer chromatography were done on EM Sciences (Cherry Hill, N.J.) types 9385, 15687, and 5717 media respectively; centrifugal chromatography was performed on 1 mm layers cast from EM Sciences 7749 silica mounted in a model 7924T Chromatotron (Harrison Research, Palo Alto, Calif.). Unless otherwise stated, temperatures are in degrees Centigrade.

N-(4-amino-2-carboxyphenyl)-aza[15]-crown-5 (1B)

2-Chloro-5-nitrobenzoic acid (Aldrich) (50.5 mg, 0.25 mmole) and 1-aza-4,7,10,13-tetraoxacyclopentadecane (46) (220 mg, 1 mmole) were heated together under reflux in pyridine (1 ml) overnight. The reaction mixture was evaporated to dryness in vacuo and purified by preparative thin layer chromatography (silica gel) to give N-(4-nitro-5-carboxyphenyl)-aza[15]-crown-5 as a yellowish brown gum (100 mg, 26% yield). NMR ($CD_3OD$, 90 MHz) δ 8.25, d, 3 Hz, 1H; 8.10, dd, 7 Hz, 3 Hz, 1H; 7.55, d, 7 Hz, 1H; 3.65, s+m, 16H; 3.20, t, 4H. The nitro-compound (60 mg) was dissolved in ethanol (2 ml) and hydrogenated at room temperature and atmospheric pressure with 15 mg palladium (5% on charcoal) catalyst. After full hydrogen uptake the mixture was filtered and the solvent evaporated in vacuo to give an off-white solid (50 mg, 94% yield) of 1B. NMR ($CD_3OD$, 90 MHz) δ 6.93, d, 7 Hz, 3 Hz, 1H; 3.50, s+m, 16H; 3.10, t, 4H.

N-(5-acetamido-8-quinolinyl)-aza[15]-crown-5 (1C)

8-Tosyloxy-5-nitroquinoline (80 mg, 0.25 mmole) [prepared by tosylation of commercial 8-hydroxy-5-nitroquinoline in pyridine] and 1-aza-4,7,10,13-tetraoxacyclopentadecane (220 mg, 1 mmole) were heated together under reflux in pyridine (2 ml) overnight. The reaction mixture was evaporated to dryness in vacuo and purified by preparative thin layer chromatography (silica gel) to give N-(5-nitro-8-quinolinyl)-aza[15]-crown-5 as a brown gum (105 mg, 25% yield). NMR ($CDCl_3$, 90 MHz) δ 8.90, dd, 9 Hz, 2 Hz, 1H; 8.45, d, 3 Hz, 1H; 8.09, d, 9 Hz, 1H; 7.25, dd, 9 Hz, 3 Hz, 1H; 6.72, d, 9 Hz, 1H; 3.72, m, 8H; 3.30, s+m, 12H. The nitro compound (50 mg) was dissolved in acetic anhydride and hydrogenated at room temperature and atmospheric pressure with 10 mg palladium (5% in charcoal) catalyst. After full hydrogen uptake the mixture was filtered and the solvent evaporated to give 1C as a brown solid (40 mg, 80%). NMR ($CD_3OD$, 90 MHz) δ 2.30, s, 3H; 3.40, m, 16H; 3.60, m, 4H; 7.20, m, 2H; 7.60, d, 9 Hz, 1H; 8.50, dd, 9 Hz, 2 Hz, 1H; 8.40, m, 1H.

N,N-bis-(5-acetamido-8-quinolinyl)-diaza[15]-crown-5 (2CC)

8-Tosyloxy-5-nitroquinoline (0.85 g, 2.5 mmole) and commercial 1,7-diaza-4,10,13-trioxacyclopentadecane (Kryptofix 21, EM Sciences) (0.19 g, 0.8 mmole) were heated together under reflux in pyridine (5 ml) overnight. The reaction mixture was evaporated to dryness in vacuo and purified by preparative thin layer chromatography (silica gel) to give N,N-bis-(5-nitro-8-quinolinyl)-diaza[15]-crown-5 as a brown gum (180 mg, 32%). NMR ($CDCl_3$, 90 MHz) δ 9.35, dd, 2 Hz, 8 Hz, 1H; 8.70, dd, 2 Hz, 3 Hz, 1H; 8.40, d, 9 Hz, 1H; 7.5, dd, 8 Hz, 3 Hz, 1H; 6.89, d, 9 Hz, 1H; 4.10, m, 6H; 3.70, s, 4H. The nitro compound (60 mg) was dissolved in acetic anhydride (2.5 ml) and hydrogenated at room temperature and atmospheric pressure with 20 mg palladium (5% on charcoal) catalyst. After full hydrogen uptake, the mixture was filtered and the solvent evaporated to give 2CC as a light brown solid (50 mg, 83%). NMR (CD$_3$OD, 90 MHz) δ 8.50, dd, 2 Hz, 8 Hz, 2H; 8.20, m, 2H; 7.85, d, 5 Hz, 2H; 7.40, m, 4H; 3.78, s, 4H; 3.48, m, 16H; 3.30, s, 6H.

N,N-bis-(5-acetamido-2-methyl-8-quinolinyl)-diaza[15]-crown-5 (2DD)

8-Tosyloxy-5-nitro-2-methylquinoline (0.8 g, 2 mmole), prepared by tosylation of 5-nitro-2-methyl-8-quinolinol (47), was heated under reflux with 1,7-diaza-4,10,13-trioxacyclopentadecane (0.110 g, 0.5 mmole) in pyridine (5 ml) overnight. The reaction mixture was evaporated to dryness in vacuo and purified by preparative thin layer chromatography (silica gel) to give N,N-bis-(5-nitro-2-methyl-8-quinolinyl)-diaza[15]-crown-5 as a reddish brown gum (85 mg, 29%). NMR (CDCl$_3$, 90 MHz) δ 9.25, d, 9 Hz, 2H; 8.45, d, 9 Hz, 2H; 7.35, dd, 9 Hz, 2 Hz, 2H; 6.85, dd, 9 Hz, 2 Hz, 2H; 4.00, m, 16H; 3.60, t, 4H; 2.62, s, 3H. The nitro compound (60 mg) was dissolved in acetic anhydride (5 ml) and hydrogenated at room temperature under atmospheric pressure with 0.02 g palladium (5% on charcoal) catalyst. After full hydrogen uptake the mixture was filtered and the solvent evaporated in vacuo to give 2DD as a brown solid (0.04 g, 78%). Mass spec. (FAB) m/e=615 (M$^+$ +1).

1,8-bis-(6-methoxy-2-methylquinolinyl-8-amino)-3,6-dioxaoctane

6-Methoxy-2-methyl-8-aminoquinoline [prepared by the method of Wan et al (21)] (3 g, 16 mmole) was dissolved in chloroform (25 ml) and triethylamine (8 ml) was added. Then 3,6-dioxaoctanedioyl chloride (22) (2.6 g, 12 mmole) in chloroform (5 ml) was added slowly with stirring under nitrogen. After 30 minutes the reaction mixture was diluted with more chloroform and washed with sodium bicarbonate solution and then brine. The chloroform solution was then passed through a plug of alumina and then evaporated in vacuo to obtain N,N-bis-(6-methoxy-2-methyl-8-quinolinyl)-3,6-dioxaoctane-1,8-diamide as a white solid (2.4 g, 60%). M.p. 191°–193°. NMR (CDCl$_3$, 90 MHz) δ 8.2, d, 3 Hz, 2H; 7.58, d, 7 Hz, 2H; 6.95, d, 7 Hz, 2H; 6.45, d, 3 Hz, 2H; 4.20, s, 4H; 3.92, s, 4H; 3.72, s, 6H; 2.50, s, 6H.

The amide (3 g, 6 mmole) was dissolved in dry tetrahydrofuran (50 ml) and aluminum hydride (23) solution (0.6M) in tetrahydrofuran (70 ml) was added slowly, and stirred over a period of two hours. Tetrahydrofuran-H$_2$O (1:1, 100 ml) was added followed by ether (200 ml). Stirring was continued for 30 more minutes and sodium hydroxide solution (20%) was added. The total reaction mixture was extracted with ether and the combined organic extracts were evaporated to dryness. The residue obtained was purified by column chromatography (silica gel, ethyl acetate:hexane:triethylamine, 75:25:1 v/v) to give the amine as a white solid (1.6 g, 57%). M.p. 89°–91°. NMR (CDCl$_3$, 90 MHz) δ 7.85, d, 7 Hz, 2H; 7.20, d, 7 Hz, 2H; 6.35, s, 2H; 3.90, s, 6H; 3.80, t, 4H; 3.50, t, 4H; 2.70, s, 6H.

N,N-bis-(6-methoxy-2-methyl-8-quinolinyl)-diaza[15]-crown-5 (2EE)

The above amine (2.25 g, 4.5 mmole) was dissolved in chloroform (200 ml) containing dimethylaniline (2.5 ml) and acylated under high dilution conditions (5 drops per second) with diglycolic acid chloride (855 mg, 5 mmole) in chloroform (200 ml). The reaction mixture was evaporated in vacuo and the residue purified by column chromatography (silica gel) to give the amide as a white solid (1.8 g, 70%). M.p. 231°–233°. NMR (CDCl$_3$, 90 MHz) δ 8.15, d, 9 Hz, 2H; 8.00, m, 2H; 7.40, d, 9 Hz, 2H; 7.30, d, 3 Hz, 2H; 4.25, s, 6H; 4.00, s+m, 20H; 2.85, s, 6H.

The macrocyclic amide (1.2 g, 2 mmole) was dissolved in dry THF (120 ml) and aluminum hydride (0.6M) in THF (25 ml) was added slowly and stirred over a period of two hours. THF-H$_2$O (1:1, 100 ml) was added, followed by ether (200 ml). Stirring was continued for 30 more minutes and sodium hydroxide solution 20% was added. The total reaction mixture was extracted with ether and the combined ether extracts were evaporated to dryness. The residue obtained was purified by column chromatography (silica gel) to give 2EE as a whitish foam (340 mg, 30%). NMR (CDCl$_3$, 90 MHz) δ 7.75, d, 9 Hz, 2H; 7.05, d, 9 Hz, 2H; 6.70, d, 3 Hz, 2H; 6.48, d, 3 Hz, 2H; 3.70, s+m, 26H; 2.50, s, 6H.

N,N-bis-(6-hydroxy-2-methyl-8-quinolinyl)-diaza15]-crown-5 (2FF)

N,N-bis-(6-methoxy-2-methyl-8-quinolinyl)-diaza[15]-crown-5 (50 mg, 0.9 mmole) was dissolved in dry tetrahydrofuran (1 ml) and added to a solution (2 ml) of diphenylphosphine 0.5 ml in 1.5 ml of dry THF and 0.35 ml of 9.5M n-butyllithium in hexane. The mixture was stirred for three hours and water was added. It was then extracted three times with chloroform-methanol 9:1 and two times with ethyl acetate. The combined organic extracts were evaporated to dryness and triturated with hexane. The residue of 2FF was purified by centrifugal chromatography with chloroform-methanol (4:1 v/v).

N,N-bis(2-(3,4-dicarboxyphenyl)-7-methylfuro [3,2-f]quinolin-5-yl)-diaza[15]-crown-5 (2GG methyl ester) (=SQFP/Me)

The above hydroxyquinoline was used directly for formylation by dissolving it in dimethylformamide (300 μl) and adding 0.5 ml of a 1:4 (v/v) mixture of POCl$_3$ and dimethylformamide. After stirring for two hours, water was added to quench the reaction mixture followed by saturated potassium carbonate to basify the solution. The reaction mixture was then extracted three times with chloroform and the combined chloroform extracts were back-washed with water and evaporated to give the salicylaldehyde as a yellow gum. The gum was purified by centrifugal chromatography with ethyl acetate to give the salicylaldehyde derivate (20 mg, 38%). NMR (CDCl$_3$, 90 MHz) δ 10.30, s, 1H (aldehyde); 8.30, d, 9 Hz, 2H; 7.15, d, 9 Hz, 2H; 6.45, s, 2H; 3.90, m, 16H; 3.60, s+m, 4H; 2.50, s, 6H.

The salicylaldehyde (10 mg, 0.017 mmole), potassium carbonate (40 mg), dimethyl 4-bromomethylphthalate (24) (14 mg, 0.05 mmole) and dimethylformamide (500 μl) were heated together at 140° (bath temperature) for four hours. The mixture was allowed to cool and chloroform with 10% methanol was added. The entire mixture was washed with water and evaporated The residue was purified by centrifugal chromatography with chloroform-methanol (9:1 v/v) to give SQPF (2GG) methyl ester a a light brown gum (5.5 g, 33%) NMR (CDCl$_3$, 200 MHz) δ 2.75, s, 6H; 3.80, s+m, 32H; 8.10, d, 2H; 7.50, d, 2H; 7.60–7.80, s+m, 8H.

N,N-bis-(1-acetamidoacridin-4-yl)-diaza[15]-crown-5 (2HH) and N,N-bis-(1-succinamidoacridin-4-yl)-diaza[15]-crown-5 (2II)

4-Methoxyacridine (1.4 g, 6.67 mmole) was dissolved in acetic anhydride (5 ml) and cooled to 0°. Concentrated nitric acid (1 eq, 0.7 ml) was added, followed by concentrated sulphuric acid (1 eq, 0.7 ml). After stirring for 1 hr, the product was filtered and the residue was extracted into methylene chloride and washed with sodium bicarbonate solution. It was then dried and evaporated in vacuo to give 1.2 g (70%) of 4-methoxy-1-nitroacridine. NMR (CDCl$_3$, 90 MHz) δ=4.20, s, 3H; 6.95, d, 9 Hz, 1H; 6.70–8.00, m, 3H; 8.34, d, 9 Hz, 1H; 8.55, d, 9 Hz, 1H; 9.82, s, 1H. The methoxy compound (500 mg) was converted to the 4-hydroxy derivative by heating with KOH (2 ml of an 11M aqueous solution) in DMSO (20 ml). This was tosylated with pyridine and toluenesulfonyl chloride to give the 4-tosyloxy derivative (260 mg, 34%). NMR (CDCl$_3$, 90 MHz) δ 2.2, s, 3H; 7.00, m, 2H, 6.30–6.80, m, 7H; 8.20, d, 9 Hz, 1H; 9.45, s, 1H. The tosyloxy compound (600 mg, 1.5 mmole) was dissolved in acetonitrile (4 ml) and 1,7-diaza-4,10,13-trioxacyclopentadecane (110 mg, 0.5 mmole) were added, followed by 1,8-bis(dimethylamino)naphthalene (290 mg, 2 mmole) and the reaction mixture heated under reflux overnight. The reaction mixture was evaporated in vacuo and the residue taken into chloroform and purified by column chromatography (silica gel, ethyl acetate, hexane 1:1) to give the N,N-bis-(1-nitro-4-acridinyl)-diaza[15]-crown-5 as a yellow gum (180 mg, 27%). NMR (CDCl$_3$, 90 MHz) δ 3.40, s, 4H; 3.82, m, 16H; 6.50, d, 9 Hz, 2H; 6.95, d, 9 Hz, 2H; 7.30, t, 9 Hz, 4H; 7.65, d, 9 Hz, 2H; 8.20, d, 9 Hz, 2H; 9.68, s, 2H.

The nitro-crown compound (70 mg, 0.1 mmole) was added to stannous chloride (200 mg in 2 ml ethanol), concentrated hydrochloric acid (3 ml), and ethanol (3 ml) and stirred overnight at room temperature. The reaction mixture was neutralized with sodium bicarbonate and extracted into chloroform. The chloroform layer was treated with acetic anhydride to give 2HH, which was purified by column chromatography (silica gel, chloroform: methanol 85:15) to a soft yellow solid (30 mg, 41.6%). NMR (CDCl$_3$, 90 MHz) δ 2.45, s, 6H; 3.55, m, 20H; 6.30, t, 4H; 6.80, t, 2H; 7.30, d, 9 Hz, 2H; 7.50, d, 9 Hz, 2H; 7.82, d, 9 Hz, 2H; 9.15, s, 2H.

The succinamide derivative (2II) was obtained by reduction of the nitro compound (45 mg, 0.064 mmole) with stannous chloride (150 mg) and conc. HCl (3 ml) in ethanol. The resulting amine hydrochloride was washed repeatedly with ethanol, dissolved in pyridine (1.5 ml), and treated with succinic anhydride with stirring. The reaction was complete in three hours and the product (2II) was purified by column chromatography (silica gel, 10% methanol in chloroform) (15 mg, reddish yellow soft solid, 28%). Mass spec. (FAB) m/e=802 (M+).

N,N-bis-(4-acetamido-2-methoxyphenyl)-diaza[15]-crown-5 (2JJ)

2-Fluoro-5-nitroanisole (26) (250 mg, 1.5 mmole) was heated under reflux with 1,7-diaza-4,10,13-trioxacyclopentadecane (108 mg, 0.5 mmole) in pyridine (5 ml) overnight. The reaction mixture was evaporated in vacuo and the residue purified by preparative thin layer chromatography (silica gel) to obtain N,N-bis-(4-nitro-2-methoxyphenyl)-diaza[15]-crown-5 as a light yellow oil (120 mg, 23%). NMR (CDCl$_3$, 90 MHz) δ 7.80, dd, 8 Hz, 3 Hz, 2H; 7.70, d, 3 Hz, 2H; 6.89, d, 8 Hz, 2H; 3.87, s, 6H; 3.68, s+m, 20H. The nitro compound (0.05 g) was dissolved in acetic anhydride and hydrogenated at room temperature and atmospheric pressure with 0.02 g palladium (5% on charcoal) catalyst. After full hydrogen uptake the mixture was filtered and the solvent evaporated in vacuo to give 2JJ as a whitish semi-solid (43 mg, 82%). Mass spec.: m/e=544 (M+); m/e =513 (M+ −OMe).

N,N-bis-(3,6-dioxocyclohexa-1,4-dienyl)-diaza[15]-crown-5 (2KK)

p-Benzoquinone (2.0 g, 18.5 mmole) and 1,7-diaza-4,10,13-trioxacyclopentadecane (400 mg, 1.8 mmole) were dissolved in a 1:1 mixture of chloroform and methanol (13 ml) and heated under reflux overnight. The reaction mixture was evaporated off in vacuo and the residue dissolved in a large volume of chloroform and filtered through a column of silica gel packed in ethyl acetate. The excess benzoquinone was removed with more ethyl acetate and the product (2KK) was obtained by eluting with 4% methanol in ethyl acetate. Evaporation of the solvent gave 2KK as a deep red foam (600 mg, 76%). NMR (CDCl$_3$, 90 MHz) δ 3.75, s, 4H; 3.88, s, 16H; 5.68, d, 1.5 Hz, 2H; 6.48, dd, 1.5 Hz, 4H.

N,N-bis-(2,5-dimethoxyphenyl)-diaza[15]-crown-5 (2LL)

The bis-quinone (2KK) (210 mg, 0.49 mmole) was dissolved in 2 ml methanol and hydrogenated with 33 mg of palladium (5% on charcoal) catalyst at atmospheric pressure and room temperature. When H$_2$ uptake ceased after 1.5 hrs, the solution had changed to a dull yellowish brown color. The reaction flask was stirred under a slight positive pressure of H$_2$ while approximately 1 mmole of tetramethylammonium hydroxide pentahydrate was injected as a 4M solution in methanol through a gas-tight rubber septum into the mixture. Then 1 mmole of neat dimethyl sulfate was similarly injected using a separate syringe. The alternate injection of tetramethylammonium hydroxide then dimethyl sulfate was repeated nine more times over the next 2.5 hrs, for a total of 10 mmoles each of base and alkylating reagent. This cyclical procedure of partial deprotonation and methylation was found to give better results than adding all the base and all the alkylating reagent simultaneously, in which case the latter two mainly destroy each other. Also by conducting the alkylation under H$_2$, the strong tendency of the phenoxide anion to re-oxidize was suppressed. Once the alkylation was complete, the product was reasonably stable to air and could be worked up by evaporating the methanol in vacuo, dissolving the residue in water, neutralizing the alkalinity with acetic acid, and extracting with chloroform. Evaporation of the chloroform gave 252 mg crude 2LL (105% of the stoichiometrically expected weight), which could be purified by centrifugal chromatography. NMR (CF$_3$COOH, 90 MHz) δ 3.95, m+s, 32H; 7.15, m, 6H.

N,N-bis-(2-methoxy-5-hydroxy-4-formylphenyl)-diaza[15]-crown-5 (2MM)

The dimethoxy compound (2LL) (30 mg, 0.06 mmole) was dissolved in dimethylformamide (200 μl) and kept at 0°. 0.5 ml of a 1:4 (v/v) mixture of POCl$_3$ and dimethylformamide was added and the reaction mixture stirred for 1 hour. Water (2 ml) was added to quench the reaction mixture followed by addition of saturated potassium carbonate to basify the solution. The reaction mixture was then extracted 3 times with chloroform. The combined chloroform extracts were back-washed with water and evaporated in vacuo to give the dimethoxyaldehyde as a yellow gum (25 mg, 75%). NMR (CDCl$_3$, 90 MHz) δ 3.80, m, 20H; 3.98, s, 6H; 4.20, s, 6H; 6.70, s, 2H; 7.48, s, 2H; 10.68, s, 2H.

The dimethoxyaldehyde (15 mg, 0.027 mmole) was dissolved in nitromethane (2 ml). Saturated zinc chloride in nitromethane solution (1 ml) was added, followed by 2 ml of 1.0M BCl$_3$ solution in dichloromethane. The reaction mixture was stirred for 1.5 hours and a 1:1 mixture of water and methanol (2 ml) was added. Stirring was continued for 30 min and potassium carbonate-EDTA solution was added. Stirring was continued for 30 more minutes and the mixture was extracted with chloroform (3 times), followed by ethyl acetate (1 time). The combined organic extracts were washed with water and purified by centrifugal chromatography on ethyl acetate to give 2MM as a yellow soft solid (11 mg, 78%). NMR (CDCl$_3$, 90 MHz) δ 3.75, m, 20H; 3.85, s, 6H; 6.50, s, 2H; 6.88, s, 2H; 9.84, s, 2H (aldehyde); 11.50, s, 1H, OH hydrogen bonded.

N,N-bis-(2-(3,4-dicarboxyphenyl)-5-methoxybenzofuran-6-yl)-diaza[15]-crown-5 (2NN Me ester) (=SBFP/Me)

The salicylaldehyde (2MM) (9 mg, 0.017 mmole), potassium carbonate (40 mg), dimethyl 4-bromomethylphthalate (11 mg, 0.04 mmole), and dimethylformamide (0.5 ml) were heated together at 140° (bath temp.) for 4 hours. The mixture was allowed to cool. Chloroform with 10% methanol (3 ml) was added. The entire mixture was washed with water and evaporated in vacuo. The residue was dissolved in 5% MeOH in chloroform and purified by centrifugal chromatography with chloroform-methanol (24:1 v/v) to give SBFP/Me as a light brown gum (5 mg, 33%). NMR (CD$_3$OD, CDCl$_3$ 1:9, 200 MHz) δ 3.70, m, 20H; 3.97, 2s, 6H; 3.99, 2s, 6H; 4.10, 2s, 6H; 7.04, m, 2H; 7.10, s, 2H; 7.85, d, 2H; 7.95, d, 2H; 8.13, s, 2H.

N,N-bis-(2-(5-carboxyoxazol-2-yl)-5-methoxybenzofuran-6-yl)-diaza[15]-crown-5 (2OO ethyl ester) (=SBFO/Et)

The salicylaldehyde (2MM) (6 mg, 0.012 mmole), potassium carbonate (40 mg), ethyl 2-chloromethyloxazole-5-carboxylate (13) (12 mg, 0.068 mmole), and dimethylformamide (300 μl) were heated together at 100° for 1 hour. The reaction mixture was allowed to cool and chloroform (3 ml) was added and the entire mixture washed with water to get rid of the solid potassium carbonate. The organic layer was evaporated in vacuo and taken into 5% methanol-chloroform for purification by centrifugal chromatography using chloroform-methanol (24:1 v/v). The product, SBFO/Et, was obtained as a yellow gum (5 mg, 57%). NMR (CD$_3$OD, CDCl$_3$ 1:9, 200 MHz) δ 1.21, t, 6H; 3.60–3.80, m, 16H; 3.98, s, 4H; 4.45, q, 4H; 4.80, d, 2H; 7.18, s, 2H; 7.55, s, 2H; 7.75, s, 2H; 7.92, s, 2H.

N,N-bis-(2-(2,4-dicarboxyphenyl)-5-methoxybenzofuran-6-yl)-diaza[15]-crown-5 (2PP methyl ester) (=SBFI/Me)

Dimethyl 4-bromomethylisophthalate was obtained by the method of Anzalone & Hirsch (24), using methanol instead of ethanol in the esterification procedure. M.p. 80°–82°. NMR (CDCl$_3$, 90 MHz) δ 3.90, s, 3H; 3.92, s, 3H; 4.90, s, 2H; 7.45, d, 7 Hz, 1H; 8.05, dd, 2 Hz, 7 Hz, 1H; 8.50, d, 2 Hz, 1H.

The above isophthalate ester (150 mg, 0.52 mmole), the salicylaldehyde 2MM (40 mg, 77 mmole), K$_2$CO$_3$ (250 mg, 1.8 mmole), and dimethylformamide (2 ml) were heated together at 150° for 2.5 hrs. The mixture was diluted with chloroform and filtered. The filtrate was washed with water and evaporated in vacuo. The gummy residue was purified by centrifugal chromatography to give SBFI/Me (28 mg, 41%). NMR (CDCl$_3$, 200 MHz) δ 3.60–3.80, m, 20H; 3.90, s, 12H; 3.95, s, 6H; 7.05, s, 2H; 7.20, s, 2H; 7.30, s, 2H; 7.80, d, 2 Hz, 2H; 8.20, dd, 7 Hz, 2 Hz, 2H; 8.35, d, 2 Hz, 2H.

N,N-bis(2-(3,4-dicarboxyphenyl)-5-methoxybenzofuran-6-yl)-diaza[18]-crown-5 (3NN Me ester) (=PBFP/Me)

The preparation of PBFP/Me was similar to that of SBFP/Me (2NN) except that 1,10-diaza-4,7,13,16-tetraoxacyclooctadecane (Kryptofix 22, EM Sciences) was used as the crown instead of 1,7-diaza-4,10,13-trioxacyclopentadecane. The properties of the various intermediates (including 3K, 3L, and 3M) and PBFP are as follows:

N,N-bis-(3,6-dioxocyclohexa-1,4-dienyl)-diaza[18]-crown-6

(3K) was obtained in 70% yield as reddish-brown needles. M.p. 153°–155°. NMR (CDCl$_3$, 90 MHz) δ 3.60–3.80, s+m, 24H; 5.60, d, 1.5 Hz, 2H; 6.48, dd, 1.5 Hz, 4H.

N,N-bis-(2,5-dimethoxyphenyl)-diaza[18]-crown-6

(3L) was obtained in 55% yield as a gum. NMR (CF$_3$COOH, 90 MHz) δ 3.40–3.80, s+m, 36H; 6.80, m, 6H.

N,N-bis-(1,4-dimethoxy-5-formyl-2-phenyl)-diaza[18]-crown-6 was obtained as an off-white soft solid. M.p. 131°–133°. NMR (CDCl$_3$, 90 MHz) δ 3.50–3.70, s+m, 24H; 3.75, s, 6H; 3.85, s, 6H; 6.50, s, 2H; 7.20, s, 2H; 10.25, s, 2H (formyl).

N,N-bis-(1-methoxy-4-hydroxy-5-formyl-2-phenyl)-diaza[18]-crown-6

(3M) was obtained as an orange solid. M.p. 134°–136°. NMR (CDCl$_3$, 90 MHz) δ 3.50–3.70, s+m, 24H; 3.75, s, 6H; 6.40, s, 2H; 6.90, s, 2H; 9.65, s, 2H (formyl); 11.40, s, 2H (hydrogen-bonded OH).

PBFP/Me (3NN methyl ester) was obtained as a light yellow gum NMR (CDCl$_3$, 200 MHz) δ]3.60, m, 8H; 3.67, m, 16H; 3.90, s, 12H; 3.93, s, 6H; 6.90, s, 2H; 7.10, s, 2H; 7.48, s, 2H; 7.68, d, 2 Hz, 2H; 7.80, dd, 2 Hz, 1 Hz, 2H; 7.98, d, 1 Hz, 2H.

Saponification of methyl or ethyl esters; preparation of acetoxymethyl ester

The esters of polycarboxylic acids 2NN, 2OO, 2PP, and 3NN were hydrolyzed by dissolving them in methanol or dioxane or a mixture of the two solvents, then adding excess base, usually tetramethylammonium hydroxide (TMA$^+$OH$^-$) or cesium hydroxide so that the cation would show negligible tendency to bind to the chelator. Acetoxymethyl (AM) esters were prepared by the standard procedure of realkylation of the polycarboxylate anions using acetoxymethyl bromide (13). A typical procedure is given below for 2PP (=SBFI) and its AM ester:

SBFI/Me (6 mg, 6.7 μmole) was dissolved in 200 μl methanol and 200 μl dioxane. 1M TMA$^+$OH$^-$ (200 μl) was added and the reaction left overnight. When hydrolysis was complete as judged by reverse-phase thin layer chromatography, the mixture was evaporated to dryness. The residue was dissolved in dimethyl-formamide (2 ml) and ethyldiisopropylamine (200) and acetoxymethyl bromide (300 μl) were added. The suspension was stirred overnight. Chloroform was added and the alkylammonium bromide salts filtered off. The filtrate was evaporated in vacuo and the residue purified by centrifugal chromatography (silica) to give the product as a hard gum (4 mg, 53%). NMR (CDCl$_3$, 200 MHz) δ 2.10, s, 6H; 2.18, s, 6H; 3.50–3.80, m, 20H; 3.88, s, 6H; 5.95, s, 4H; 6.05, s, 4H; 6.98, s, 2H; 7.05, s, 2H; 7.20, s, 2H; 7.87, d, 7 Hz, 2H; 8.20, dd, 7 Hz, 2 Hz, 2H; 8.35, d, 2 Hz, 2H.

REFERENCES

The present specification refers to the following publications, each of which is expressly incorporated by reference herein.

1. Skou, J. C., Norby, J. G., Maunsback, A. B., and Esmann, M., eds., (1988) *The Na+, K+-Pump, Part B: Cellular Aspects* in *Progr. Clin. Biol. Res.*, Vol. 268, A. R. Liss, New York.
2. Guernsey, D. L., and Edelman, I. S., (1983) in *Molecular Basis of Thyroid Hormone Action* (J. H. Oppenheimer and H. H. Samuels, eds.), pp. 293–324, Academic Press, New York.
3. Dix, J.-P. and Vögtle, F., (1980) *Chem. Berichte* 113457–470.
4. Löhr, H. G., and Vögtle, F., (1985) *Acc. Chem. Res.* 18, 65–72.
5. Lehn, J. M., and Sauvage, J. P., (1975) *J. Am. Chem. Soc.* 97, 6700–6707.
6. Smith, G. A., Morris, P. G., Hesketh, T. R., and Metcalfe, J. C., (1986) *Biochem. Biophys. Acta* 889, 72–83.
7. Smith, G. Z., Hesketh, T. R., and Metcalfe, J. C., (1988) *Biochem. J.* 227–232.
8. Cram, D. J., (1983) *Science* 219, 1177–1183.
9. Cram, D. J., Carmack, R. A., and Helgeson, R. C., (1988) *J. Am. Chem. Soc.* 10, 571–577.
10. Harootunian, A. T., Kawanishi, T., Kao, J. P. Y., Eckert, B. K., and Tsien, R. Y., (1989) Journal of Biological Chemistry 264, 19458–19467.
11. Moore, E. D. W., Tsien, R. Y., Minta, A., and Fay, F. S., (1988) *FASEB J.* 2, A754.
12. Negulescu, P. A., Harootunian, A. T., Minta, A., Tsien, R. Y., and Machen, T. E., (1988) *J. Gen. Physiol.* 92, 26a.
13. Grynkiewicz, G., Poenie, M., and Tsien, R. Y., (1985) *J. Biol. Chem.* 260, 3440–3450.
14. Tsien, R. Y., Pozzan, T., and Rink, T. J., (1982) *J. Cell Biol.* 94, 325–334.
15. Rossotti, H., (1989) *The Study of Ionic Equilibria*. Longman, London.
16. Tsien, R.Y., (1980) *Biochemistry* 19, 2396–2404.
17. Vögtle, F., and Weber, E., (1980) in *The Chemistry of Ethers, Crown Ethers, Hydroxyl Groups and Their Sulphur Analogues*, Supplement E, part 1, (S. Patai, ed.), pp. 59–156, John Wiley, New York.
    Tsien, R. Y., (1983) *Annu. Rev. Biophys. Bioeng.* 12, 91–116.
19. Wun, T.-C., Bittman, R., and Borowitz, I. J., (1977) *Biochemistry* 16, 2074–2079.
20. Tramer, A., (1969) *J. Mol. Struct.* 4, 313–325.
21. Wan, Y. P., Porter, T. H., and Folkers, K., (1974) *J. Heterocyclic Chem.* 11, 519–524.
22. Dietrich, B., Lehn, J. M., Sauvage, J. P., and Blanzat, J., (1973) *Tetrahedron* 29, 1629–1645.
23. Yoon, N. M., and Brown, H. C., (1968) *J. Am. Chem. Soc.* 90, 2927–2938.
24. Anzalone, L., and Hirsch, J. A., (1985) *J. Org. Chem.* 50, 2128–2133.
25. Irving, H., Butler, E. J., and Ring, M. F., (1949) *J. Chem. Soc.* 1949, 1489–1498.
26. Ruyle, W. V., Sarett, L. H., and Matzuk, A. R., (1977) U.S. Pat. No. 4,044,049.
27. Hikosaka, A., (1970) *Bull. Chem. Soc. Japan* 43, 3928–3929.
28. Ulrich, H., and Richter, R., (1977) in *Methoden der Organischen Chemie (Houben-Weyl)*, Vol. VII/3a, pp. 404–412, Georg Thieme, Stuttgart.
29. Dean, F. M., Goodchild, J., Houghton, L. E., Martin, J. A., Morton, R. B., Parton, B., Price, A. W., and Somvichien, N., (1966) *Tetrahedron Lett.* 4153–4159.
30. Somlyo, A. P., ed. (1986) *Recent Advances in Electron and Light Optical Imaging in Biology and Medicine* (Ann. N.Y. Acad, Sci., Vol. 483), New York Academy of Sciences, N.Y.
31. Horowitz, S. B., and Paine, P. L., (1979) *Biophys. J.* 25, 45–62.
32. Slack, C., Warner, A. E., and Warren, R. L., (1973) *J. Physiol. (London)* 232, 297–312.
33. Springer, C. S., Jr., (1987) *Ann. N.Y. Acad. Sci.* 508, 130–148.
34. Liebling, M. S., and Gupta, R. K., (1987) *Ann. N.Y. Acad. Sci.* 508, 149–163.
35. Tsien, R. Y., (1986) in *Optical Methods in Cell Physiology* (P. de Weer and B. M. Salzberg, eds.) pp. 327–345, Wiley Interscience, N.Y.
36. Gramain, P., and Frère, Y., (1979) *Nouv. J. Chimie* 3, 53–58.
37. Nakatsuji, Y., Nakamura, T., Yonetani, M., Yuya, H., and Okahara, M., (1988) *J. Am. Chem. Soc.* 110, 531–538.
38. Takagi, M., and Ueno, K., (1984) *Topics Curr. Chem.* 121, 39–65.
39. Shiga, M., Nishida, H., Nakamura, H., Takagi, M., and Ueno, K., (1983) *Bunseki Kagaku* 32, E293–E300.
40. Tazaki, M., Nita, K., Takagi, M., and Ueno, K., (1982) *Chem. Lett.* 571–574.
41. Chang, C. A., and Ochaya, V. O. (1986) *Inorg. Chem.* 25, 355–358.
42. Gandour, R. D., Fronczek, F. R., Gatto, V. J., Minganti, C., Schultz, R. A., White, B. D., Arnold, K. A., Mazzochi, D., Miller, S. R., and Gokel, G. W., (1986) *J. Am. Chem. Soc.* 108, 4078–4088.

43. Gatto, V. J., Arnold, K. A., Viscariello, A. M., Miller, S. R., Morgan, C. R., and Gokel, G. W., (1986) *J. Org. Chem,* 51, 5373-5384.
44. Thomas, R. C., and Cohen, C. J., (1981) *Pfugers Arch.* 390, 96-98.
45. Lein, G. M., and Cram, D. J., (1982) *J. Chem. Soc., Chem. Commun.* 301-304.
46. Maeda, H., Furuyoshi, S., Nakatsuji, Y., and Okahara, M., (1983) *Bull. Chem. Soc. Jpn.* 56, 212-218.
47. Perez-Cistue, J. I. C., (1956) *Rev. acad. cienc. exact. fis.-quim. y. nat. Zaragosa* 11, 33-87. [Chem. Abst. (1958) 52, 13544-13545.]
48. Weber, E. and Vögtle, F., (1976) *Chem. Ber.* 109, 1803-1831.
49. Laidler, D. Z., and Stoddart, J. F., (1980) in *The Chemistry of Ethers, Crown Ethers, Hydroxyl Groups and Their Sulphur Analogues,* Supplement E, Part 1, (S. Patai, ed.), pp. 1-58, John Wiley, New York.
50. Nakatsuji, Y., Nakamura, T., Okahara, M., Dishong, D. M., and Gokel, G. W., (1983) *J. Org. Chem.* 48, 1237-1242.
51. Tsien, R. Y. (1981) *Nature* 290, 527-528.
52. Minta, A. M. and Tsien, R. Y., (1989) *J. Biol. Chem* 264, 19449-19457.

SPECIFICATION SUMMARY

From the foregoing description, one of ordinary skill in the art can understand that the present invention provides new macrocyclic fluorescent chelating compounds for alkali metal cations. The new chelating compounds are comprised of: (1) crown ethers (that may or may not have substituent groups attached to the core carbons, but will always contain at least one core nitrogen) that are linked via the core nitrogen(s) to at least one (2) fluorophore that contains heteroaromatic ligands. The new fluorescent indicator compounds are used to nondestructively observe intracellular alkali metal cations such as cytosolic concentrations of free $Na^+$, $K^+$, and $Li^+$. Tests in lymphocytes, hepatocytes, fibroblasts, smooth muscle cells, and gastric glands demonstrate the biological utility of the macrocyclic compounds of the present invention for nondestructive observation of $[Na^+]_i$ in individual cells viewed by fluorescence microscopy.

Without departing from the spirit and scope of this invention, one of ordinary skill can make various changes and modifications to the invention to adapt it to various usages and conditions. As such, these changes and modifications are properly, equitable, and intended to be, within the full range of equivalence of the following claims.

What is claimed is:

1. The compound SBFI, having the structure:

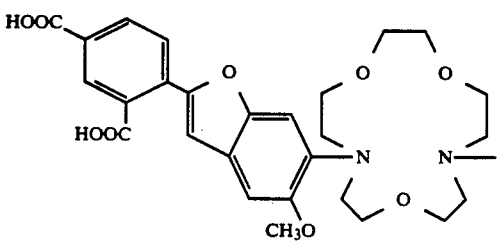

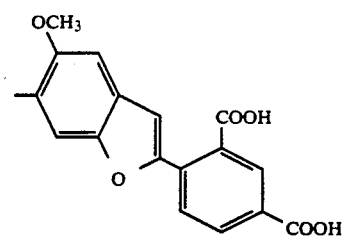

and the physiologically acceptable non-toxic esters and salts thereof.

2. The compound PBFI, having the structure:

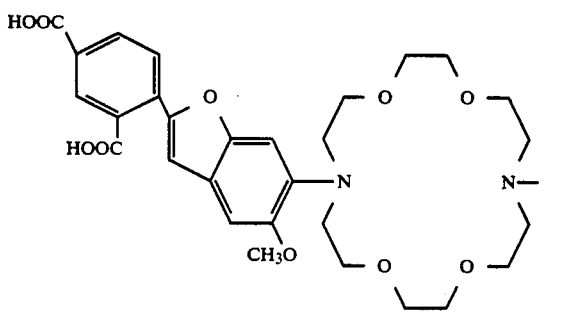

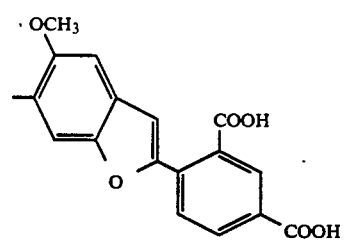

and the physiologically acceptable non-toxic esters and salts thereof.

3. The compound of claim 1 as the physiologically acceptable non-toxic ester.

4. The compound of claim 3 as the physiologically acceptable non-toxic acetoxymethyl ester.

5. The compounds of claim 1 as the physiologically acceptable non-toxic salt.

6. The compound of claim 2 as the physiologically acceptable non-toxic free acid.

7. The compound of claim 2 as the physiologically acceptable non-toxic ester.

8. The compound of claim 7 as the physiologically acceptable non-toxic acetoxymethyl ester.

9. The compounds of claim 2 as the physiologically acceptable non-toxic salt.

10. A compound or the physiologically acceptable non-toxic methyl, ethyl or acetoxylmethyl esters or salts thereof wherein said compound is selected from the group consisting of:

(a)
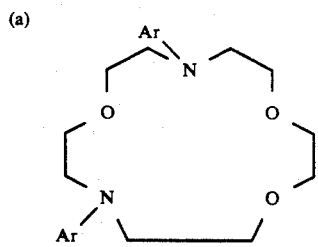
2
wherein Ar groups in structure 2 are identical and are selected from the group consisting of:
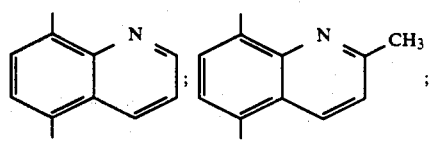
C         D
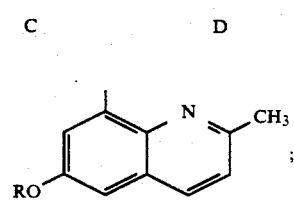
R = CH₃ or H
E         F
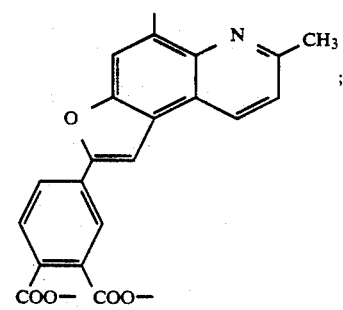
G
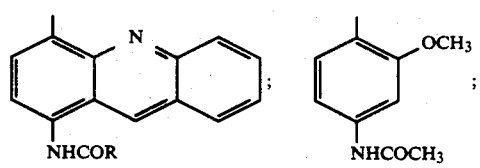
R = CH₃ or —CH₂CH₂COO—
H          I          J
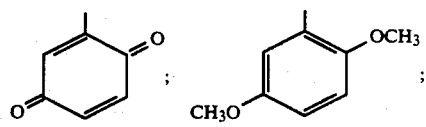
K         L
-continued
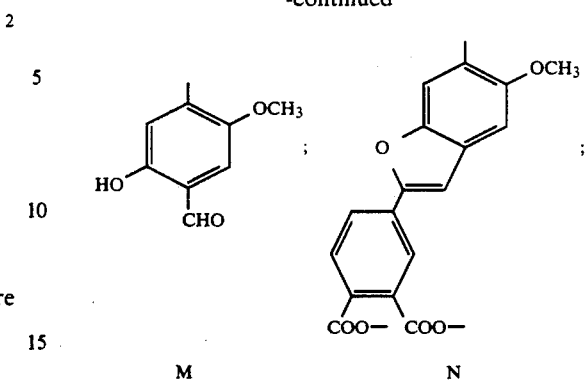
M         N
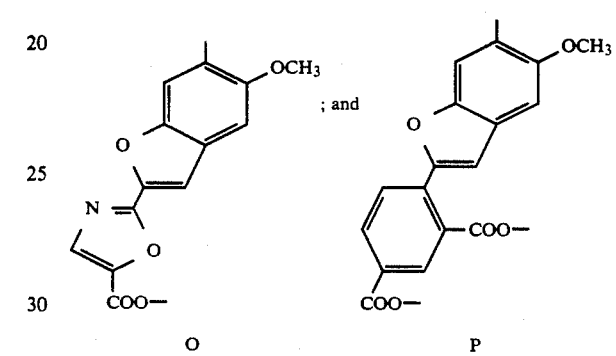
; and
O         P
and;
(b)
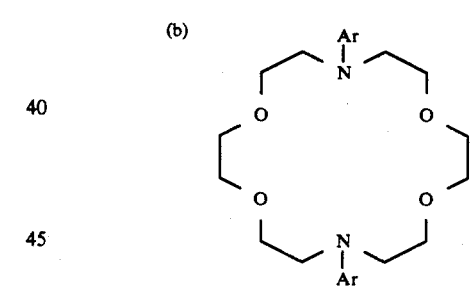
3
wherein the Ar groups in structure 3 are identical and are selected from the group consisting of
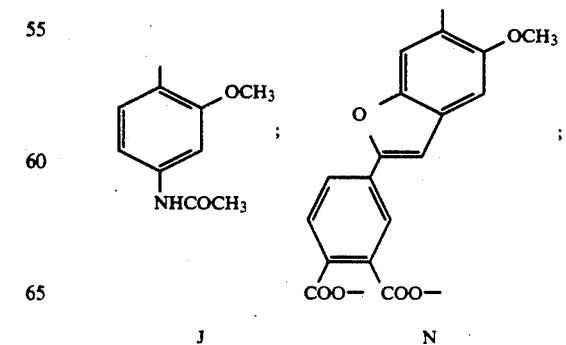
J         N

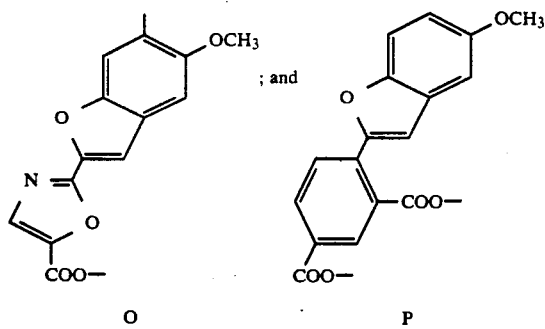

O  P

11. The compound of claim 10 as the physiologically acceptable non-toxic free acid.

12. The compound of claim 10 as the physiologically acceptable non-toxic ester.

13. The compound of claim 10 as the physiologically acceptable non-toxic acetoxymethyl ester.

14. The compound of claim 10 as the physiologically acceptable non-toxic salt.

15. A compound or the pharmaceutically acceptable physiologically hydrolyzable esters or salts thereof, wherein said compound is selected from the group consisting of:

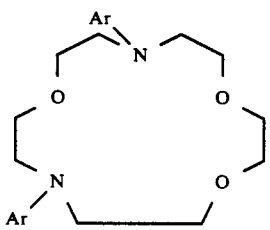

(aa)  2 wherein the Ar groups in structure 2 are not identical and are selected from the group consisting of:

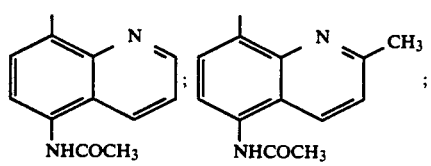

C  D

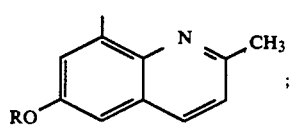

R = CH$_3$ or H

E  F

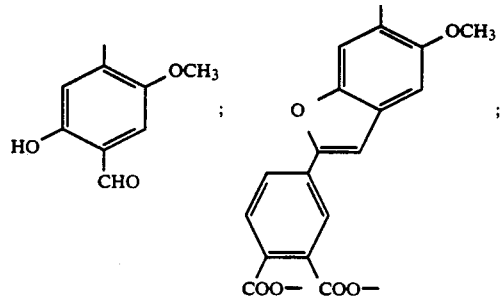

G

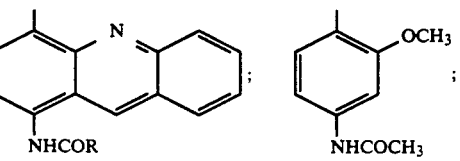

R = CH$_3$ or CH$_2$CH$_2$COO—

H  I  J

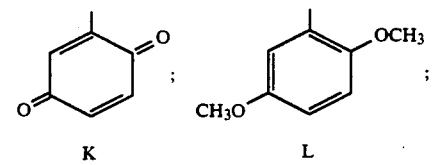

K  L

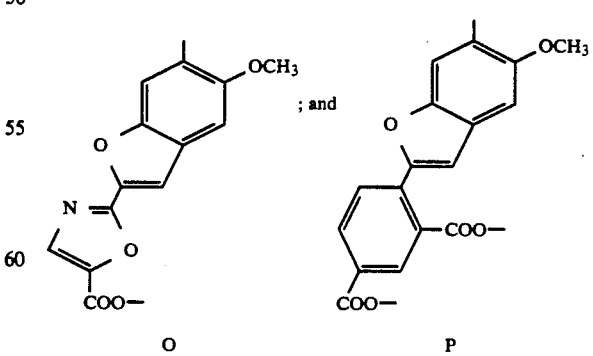

M  N

; and

O  P with the proviso that when one Ar group is selected from C, D, E, F, G or H, the other Ar group is selected from J, K, L, M, N, O or P; and (bb)

[Structure 3: macrocyclic diaza-tetraoxa ring with two Ar groups on N atoms]

wherein the Ar groups in structure 3 are not identical and are selected from the group consisting of:

[Structures C and D: quinoline derivatives with NHCOCH₃]

C    D

[Structure with RO group on quinoline, R = CH₃ or H]

E   F

[Structure G: benzofuran-quinoline with two COO— groups]

G

[Structures H, I: acridine with NHCOR, R = CH₃ or CH₂CH₂COO—]

[Structure J: methoxy-NHCOCH₃ aryl]

H   I   J

[Structures K, L: quinones and dimethoxy benzene]

K   L

[Structure M: hydroxy-methoxy-CHO benzene]

[Structure N: benzofuran with OCH₃ and two COO— groups]

M   N

[Structure O: with N, O, COO—]; and [Structure P: benzofuran with OCH₃ and two COO—]

O   P with the proviso that when one Ar group is selected from group C, D, E, F, G and H, the other Ar group is selected from group J, K, L, M, N, O or P.

16. The compound of claim 15 as the physiologically acceptable non-toxic free acid.

17. The compound of claim 15 as the physiologically acceptable non-toxic ester.

18. The compound of claim 15 as the physiologically acceptable non-toxic acetoxymethyl ester.

19. The compound of claim 15 as the physiologically acceptable non-toxic salt.

20. The compound of claim 15 wherein one Ar group is selected from groups C, D, E, F, G, H or I, the other group is selected from groups N, O or P.

21. The compound of claim 20 as the physiologically acceptable non-toxic free acid.

22. The compound of claim 20 as the physiologically acceptable non-toxic ester.

23. The compound of claim 20 as the physiologically acceptable non-toxic acetoxymethyl ester.

24. The compound of claim 20 as the physiologically acceptable non-toxic salt.

* * * * *